US009112232B2

(12) United States Patent
Choi et al.

(10) Patent No.: US 9,112,232 B2
(45) Date of Patent: Aug. 18, 2015

(54) COMPOSITION, POLYMER THEREOF, ELECTRODE AND ELECTROLYTE MEMBRANE FOR FUEL CELL, AND FUEL CELL INCLUDING THE SAME

(75) Inventors: Seong-woo Choi, Yongin-si (KR); Jung-ock Park, Yongin-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 740 days.

(21) Appl. No.: 13/020,385

(22) Filed: Feb. 3, 2011

(65) Prior Publication Data

US 2011/0195340 A1   Aug. 11, 2011

(30) Foreign Application Priority Data

Feb. 5, 2010 (KR) .......................... 10-2010-0011179
Jan. 21, 2011 (KR) .......................... 10-2011-0006492

(51) Int. Cl.
 C08F 26/06 (2006.01)
 H01M 4/86 (2006.01)
 H01M 8/10 (2006.01)

(52) U.S. Cl.
 CPC ............ H01M 4/8668 (2013.01); H01M 8/103 (2013.01); H01M 8/1027 (2013.01); Y02E 60/521 (2013.01)

(58) Field of Classification Search
 USPC ................................... 429/492, 530; 526/260
 See application file for complete search history.

(56) References Cited

U.S. PATENT DOCUMENTS

| 4,772,678 | A | 9/1988 | Sybert et al. |
| 5,723,086 | A * | 3/1998 | Ledjeff et al. ................. 264/248 |
| 2005/0256296 | A1 * | 11/2005 | Kiefer et al. ................. 528/327 |
| 2006/0211844 | A1 | 9/2006 | Kim et al. |
| 2007/0020507 | A1 | 1/2007 | Kim et al. |
| 2007/0184323 | A1 * | 8/2007 | Lee et al. .......................... 429/33 |
| 2008/0145743 | A1 * | 6/2008 | Choi et al. ....................... 429/43 |
| 2009/0098437 | A1 | 4/2009 | Choi et al. |
| 2009/0117436 | A1 | 5/2009 | Choi et al. |
| 2010/0159347 | A1 | 6/2010 | Choi et al. |

FOREIGN PATENT DOCUMENTS

| JP | 8-504293 | 5/1996 |
| JP | 11-97011 | 4/1999 |
| JP | 2003-255487 | 9/2003 |
| JP | 2003-257491 | 9/2003 |
| JP | 2005-85638 | 3/2005 |
| JP | 2007-188753 | 7/2007 |
| JP | 2007-519183 | 7/2007 |

(Continued)

OTHER PUBLICATIONS

Stephen J. Krause et al., "Morphology and mechanical properties of a phase separated and a molecular composite 30% PBT/70% ABPBI triblock copolymer", *Polymer*, 1988, vol. 29, pp. 195-206.

(Continued)

*Primary Examiner* — Peter D Mulcahy
*Assistant Examiner* — Henry Hu
(74) *Attorney, Agent, or Firm* — Cantor Colburn LLP

(57) ABSTRACT

A composition including a compound having a fluorine functional group, a polymer as a polymerization product of the composition, an electrode and an electrolyte membrane for a fuel cell, which include the composition or the polymer thereof, and a fuel cell including at least one of the electrode and the electrolyte membrane.

16 Claims, 7 Drawing Sheets

(56) References Cited

FOREIGN PATENT DOCUMENTS

| | | |
|---|---|---|
| KR | 10-2006-0001625 | 1/2006 |
| KR | 10-2006-0100689 | 9/2006 |
| KR | 10-2006-0108792 | 10/2006 |
| KR | 1020070025626 A | 3/2007 |
| KR | 1020070025627 A | 3/2007 |
| KR | 10-2007-0080483 | 8/2007 |
| KR | 2007-0080483 A * | 8/2007 |
| KR | 10-2008-0008754 | 1/2008 |
| KR | 10-0829554 | 5/2008 |
| KR | 10-2008-0055510 | 6/2008 |
| KR | 2008-0055510 A * | 6/2008 |
| KR | 10-2009-0027183 | 3/2009 |
| KR | 10-2009-0037117 | 4/2009 |
| KR | 10-2009-0045655 | 5/2009 |
| KR | 10-2010-0069625 | 6/2010 |
| WO | WO 2005/060444 | 7/2005 |
| WO | WO 2005/063852 | 7/2005 |

OTHER PUBLICATIONS

Yi-Che Su et al., "Synthesis and characterization of fluorinated polybenzoxazine material with low dielectric constant", *Polymer 44* (2003) pp. 7989-7996.

Juan Antonio Asensio et al., "Polymer Electrolyte Fuel Cells Based on Phosphoric Acid-Impregnated Poly (2, 5-benzimidazole) Membranes", *Journal of the Electrochemical Society*, 151 (2004), pp. A304-A310.

Hyoung-Juhn Kim et al., "Polybenzimidazoles for High Temperature Fuel Cell Applications", *Macromolecular Rapid Commun.* 2004, 25, pp. 1410-1413.

Palanichamy Krishnan et al., "Performance of a poly(2,5-benzimidazole) membrane based high temperature PEM fuel cell in the presence of carbon monoxide", *Journal of Power Sources 159* (2006), pp. 817-823.

Jeong-Hi Kim et al., "Dependence of the performance of a high-temperature polymer electrolyte fuel cell on phosphoric acid-doped polybenzimidazole ionomer content in cathode catalyst layer", *Journal of Power Sources 170* (2007), pp. 275-280.

C. Wannek et al., "Durability of ABPBI-based MEAs for High Temperature PEMFCs at Different Operating Conditions", *Fuel Cells 08*, 2008, No. 2, pp. 87-95.

U.S. Appl. No. 13/019,591, filed Feb. 2, 2011, Seong-woo Choi et al.
U.S. Appl. No. 13/019,625, filed Feb. 2, 2011, Seong-woo Choi et al.
U.S. Appl. No. 13/020,035, filed Feb. 3, 2011, Seong-woo Choi et al.
U.S. Appl. No. 13/039,745, filed Mar. 3, 2011, Jung-ock Park et al.

* cited by examiner

COMPOSITION, POLYMER THEREOF, ELECTRODE AND ELECTROLYTE MEMBRANE FOR FUEL CELL, AND FUEL CELL INCLUDING THE SAME

CROSS-REFERENCE TO RELATED APPLICATIONS

This application claims the benefit of Korean Application Nos. 10-2010-0011179, filed Feb. 5, 2010, and 10-2011-0006492, filed Jan. 21, 2011, both filed in the Korean Intellectual Property Office, the disclosures of which are incorporated herein by reference.

BACKGROUND

1. Field

Aspects of the present disclosure relate to a composition including a compound having a fluorine functional group, a polymer of the composition, an electrode and an electrolyte membrane for a fuel cell that include the composition or the polymer, and a fuel cell including at least one of the electrode and the electrolyte membrane.

2. Description of the Related Art

Fuel cells that include a polymer electrolyte membrane operate at relatively low temperatures and may be manufactured in small sizes. Thus, such fuel cells are expected to be used as energy sources in electric vehicles and in distributed generation systems. Perfluorocarbon sulfonic acid-based polymer membranes, such as NAFION membranes (available from E.I. du Pont de Nemours and Company), are commonly used as polymer electrolyte membranes for fuel cells.

However, such polymer electrolyte membranes should be humidified in order to sufficiently conduct protons. In addition, to enhance cell system efficiencies, polymer electrolyte membranes should be operated at high temperatures, i.e., at least 100° C. However, the moisture in the polymer electrolyte membrane is evaporated and depleted at such temperatures, which reduces the effectiveness thereof.

To address such problems and/or other problems in the related art, non-humidified electrolyte membranes, which may operate at temperatures of at least 100° C. without humidification, have been developed. For example, polybenzimidazole doped with phosphoric acid has been disclosed as a material for a non-hydrated electrolyte membrane.

In low temperature perfluorocarbonsulfonate polymer electrolyte membrane fuel cells, in order to prevent defective gas diffusion in an electrode (in particular in a cathode), which may be caused by water (product water) generated during electric power production in the electrode, hydrophobic electrodes including polytetrafluoroethylene (PTFE) have been used.

In addition, phosphoric acid fuel cells, which operate at temperatures of from 150 to 200° C., include a liquid phosphoric acid electrolyte. However, the liquid phosphoric acid included in a large amount in electrodes interferes with gas diffusion in the electrodes. Therefore, an electrode catalyst layer that includes a polytetrafluoroethylene (PTFE) waterproofing agent, which prevents fine pores in the electrodes from being clogged by the phosphoric acid, has been used.

In addition, in fuel cells including a polybenzimidazole (PBI) electrolyte membrane, which uses a phosphoric acid as a non-humidified electrolyte, in order to reduce contact between electrodes and the electrolyte membrane, a method of impregnating the electrodes with a liquid phosphoric acid has been used, and a method of increasing the loading amount of metal catalysts has been used. However, such fuel cells do not exhibit improved properties.

In addition, when a phosphoric acid-doped solid polymer electrolyte is used, and air is supplied to the cathode, the activation time thereof is about 1 week, even when an optimized electrode composition is used. Although the performance of the solid polymer electrolyte may be improved, and the activation time may be shortened, as air supplied to the anode is replaced with oxygen, this replacement is undesirable for commercial use. Furthermore, an electrolyte membrane prepared using a homopolymer of PBI does not have sufficient mechanical properties, chemical stability, and capability to retain phosphoric acid at a high temperature.

SUMMARY

Provided are a composition having improved oxygen permeability, a polymer of the composition, a method of preparing the polymer, an electrode and an electrolyte membrane for a fuel cell that include the composition or the polymer thereof, and a fuel cell including at least one of the electrode and the electrolyte membrane.

According to an aspect of the present invention, a composition includes at least one compound selected from among a compound represented by Formula 1 below and a compound represented by Formula 2 below:

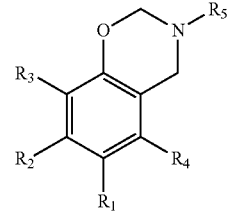

Formula 1

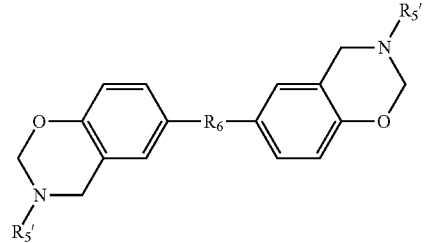

Formula 2 wherein, in Formulae 1 and 2, $R_1$ through $R_4$ are each independently a hydrogen atom, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_2$-$C_{20}$ heteroaryl group, a substituted or unsubstituted $C_2$-$C_{20}$ heteroaryloxy group, a substituted or unsubstituted $C_4$-$C_{20}$ carbocyclic group, a substituted or unsubstituted $C_4$-$C_{20}$ carbocyclic oxy group, a substituted or unsubstituted $C_2$-$C_{20}$ heterocyclic group, a substituted or unsubstituted $C_2$-$C_{20}$ heterocyclicoxy group, a halogen atom, a hydroxyl group, or a cyano group;

$R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(=O)—, and —SO$_2$—; and $R_5$ and $R_5'$ are each independently —(CF$_2$)$_n$—CF$_3$ or a group represented by Formula 3 below, wherein n is an integer from 1 to 20, and

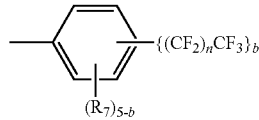

Formula 3 wherein, in Formula 3, n is an integer from 1 to 20, and b is an integer from 1 to 5; and $R_7$ is identical or different from each other and is selected from among a hydrogen atom, fluorine, a C1-C20 alkyl group, a fluorinated C1-C20 alkyl group, a C6-C20 aryl group, and a fluorinated C6-C20 aryl group.

Another aspect of the present invention provides a polymer that is a polymerization product of the composition described above.

According to another aspect of the present invention, an electrode for a fuel cell includes the composition described above or the polymer described above.

According to another aspect of the present invention, an electrolyte membrane for a fuel cell includes the composition described above or the polymer described above.

According to another aspect of the present invention, a fuel cell includes: a cathode; an anode; and an electrolyte membrane disposed between the cathode and the anode, wherein at least one of the cathode, the anode and the electrolyte membrane includes the composition described above or the polymer described above.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings, of which.

DETAILED DESCRIPTION

Figure 1:
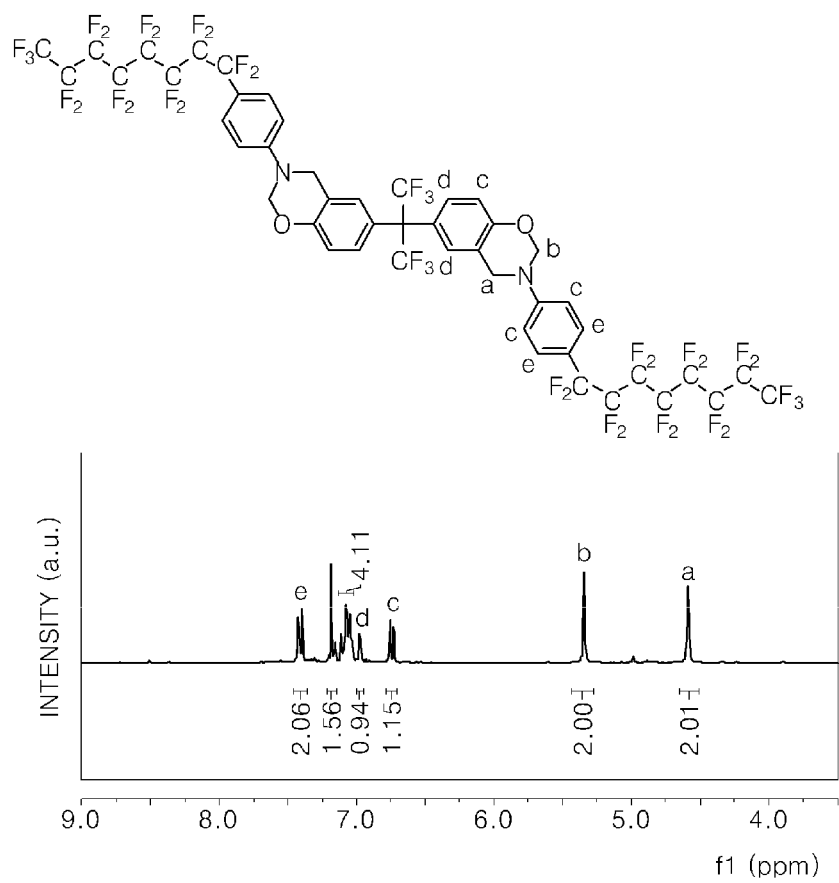
FIGS. 1 through 3 are, respectively, 1H-nuclear magnetic resonance (1H-NMR), 13C-NMR and 19F-NMR spectra of the compound of Formula 8 prepared in Synthesis Example 1.

Reference will now be made in detail to the present embodiments of the present invention, examples of which are illustrated in the accompanying drawings. The embodiments are described below in order to explain the present invention by referring to the figures.

According to an aspect of the present invention, a composition includes at least one compound selected from among a compound represented by Formula 1 below and a compound represented by Formula 2 below.

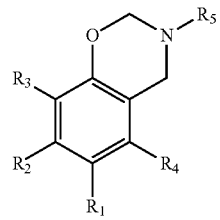

Formula 1

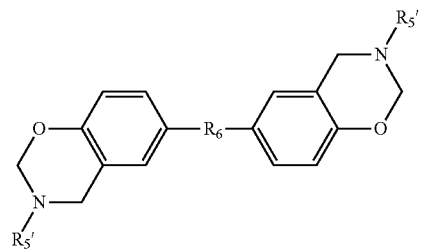

Formula 2

In Formulae 1 and 2, $R_1$ through $R_4$ are each independently a hydrogen atom, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_2$-$C_{20}$ heteroaryl group, a substituted or unsubstituted $C_2$-$C_{20}$ heteroaryloxy group, a substituted or unsubstituted $C_4$-$C20$ carbocyclic group, a substituted or unsubstituted $C_4$-$C_{20}$ carbocyclic oxy group, a substituted or unsubstituted $C_2$-$C_{20}$ heterocyclic group, a substituted or unsubstituted $C_2$-$C_{20}$ heterocyclicoxy group, a halogen atom, a hydroxyl group, or a cyano group;

$R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(=O)—, and —SO$_2$—; and $R_5$ and $R_{5'}$ are each independently —$(CF_2)_n$—$CF_3$ where n is an integer from 1 to 20, or a group represented by Formula 3 below where n is an integer from 1 to 20.

Formula 3

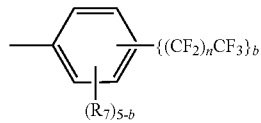

In Formula 3, n is an integer from 1 to 20, and b is an integer from 1 to 5; and $R_7$ is identical or different from each other R and is selected from among a hydrogen atom, fluorine, a $C_1$-$C_{20}$ alkyl group, a fluorinated $C_1$-$C_{20}$ alkyl group, a $C_6$-$C_{20}$ aryl group, and fluorinated $C_6$-$C_{20}$ aryl group.

In some embodiments, $R_5$ and $R_{5'}$ in Formulae 1 and 2 above may be each independently —$(CF_2)_n$—$CF_3$ where n is an integer from 5 to 15, or a group represented by Formula 3 above where n is an integer from 5 to 15.

When an electrode for fuel cells is manufactured using a compound including the above-listed substituents for $R_5$ and $R_{5'}$, the electrode may have improved oxygen permeability.

When the composition includes both the compound of Formula 1 and the compound of Formula 2, the amount of the compound of Formula 2 may be in the range of about 0.1 to about 99.9 parts by weight based on 100 parts by weight of the compound of Formula 1.

The composition may be used in forming an electrode and an electrolyte membrane for fuel cells.

Another aspect of the present invention provides a polymer that is a product of polymerization of the composition.

In Formula 3, when b is 5, $(R_7)_0$ is a hydrogen atom.

Examples of the fluorinated $C_1$-$C_{20}$ alkyl group include $CF_3$, $CF_2CF_3$, and the like.

In Formula 3, n may be an integer from 1 to 14.

The polymer includes a phenyl group having a perfluorinated long-chain alkyl group at the 4-position of the phenyl group, as represented in Formula 3 above, as $R_5$ and $R_{5'}$, and thus has higher oxygen solubility.

Examples of the compound of Formula 2 include compounds represented by Formulae 4 through 7 below:

Formula 4

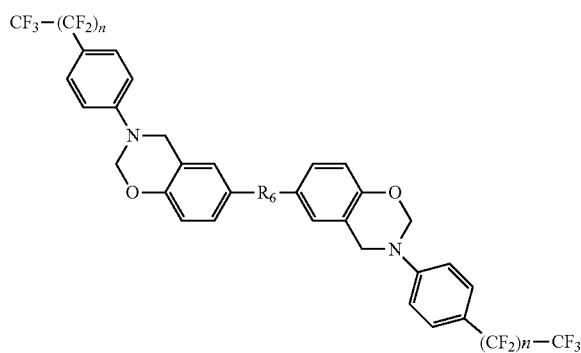

Formula 5

Formula 6

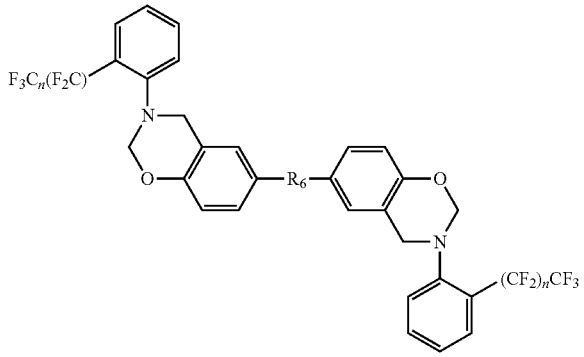

Formula 7

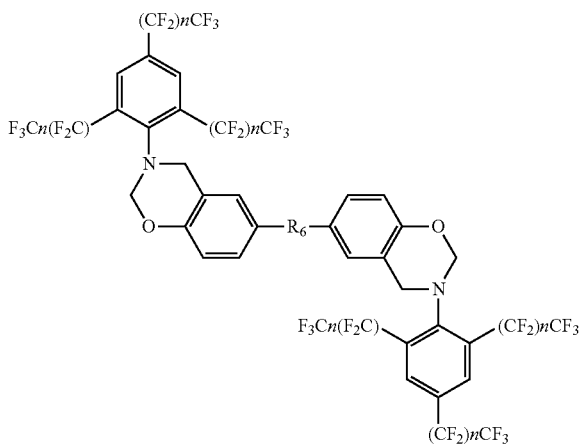

In Formulae 4 through 7, n may be an integer from 1 to 20; and $R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(=O)—, —O—, and —$SO_2$—.

For example, in Formulae 4 through 7, $R_6$ may be —C(CF_3)_2—, —SO_2—, —C(=O)—, —C(CH_3)_2—, or —O—. For another example, in Formulae 4 through 7, n may be an integer from 5 to 15.

Examples of the compounds of Formulae 4 through 7 include compounds represented by Formulae 8 through 11 below:

Formula 8

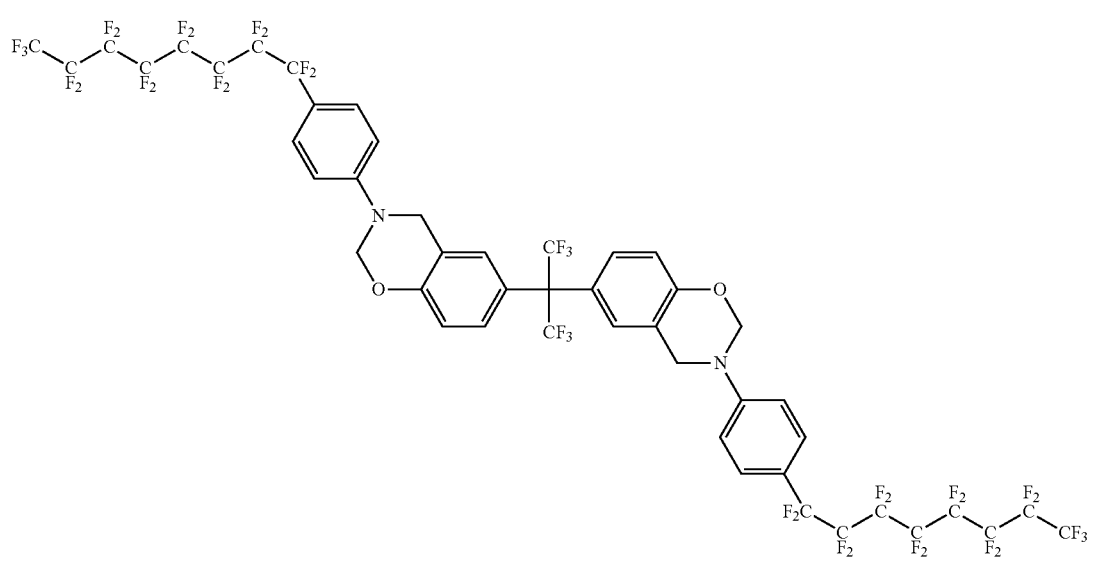

Formula 9

Formula 10

Formula 11

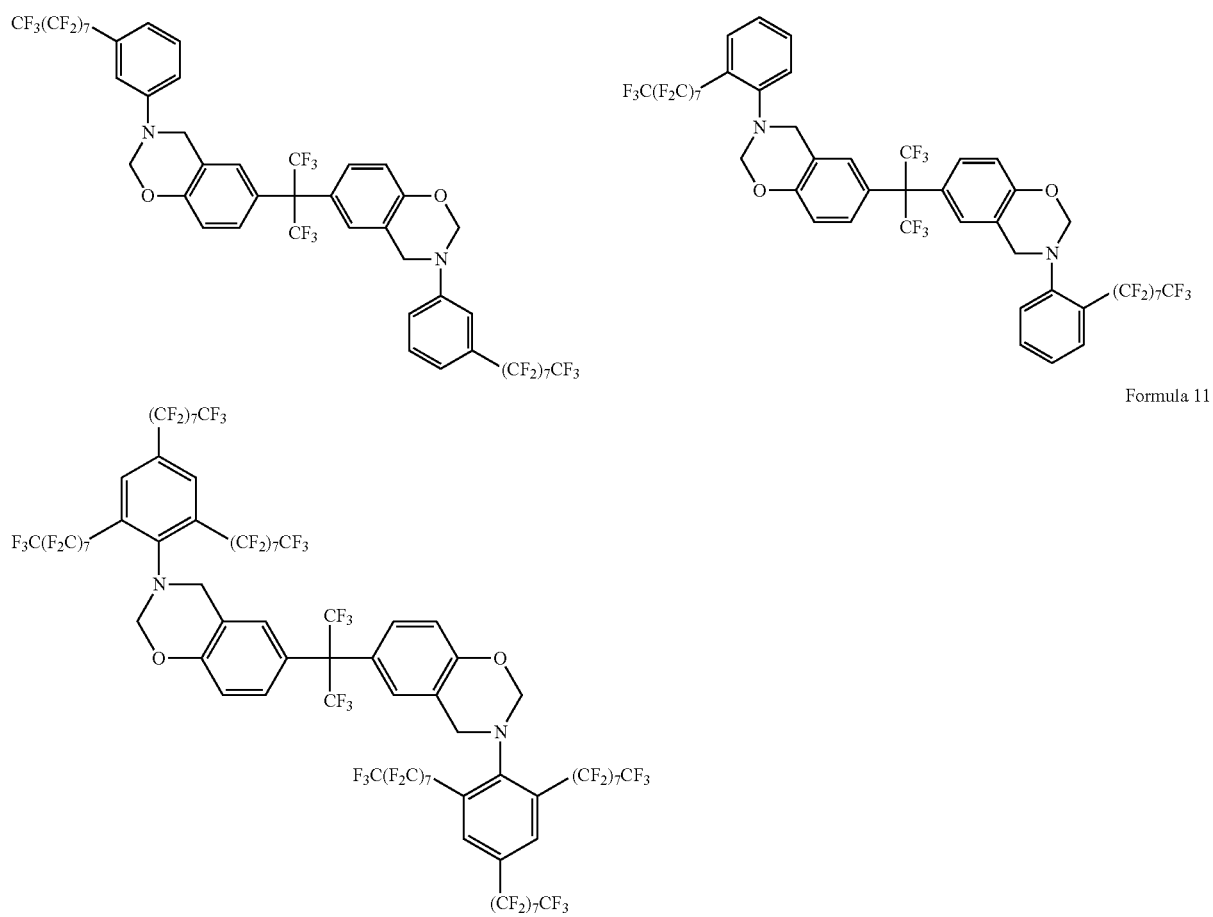

The compounds of Formulae 8 through 11 include a phenyl group having at least one perfluorinated octyl group. Thus, when the compounds of Formulae 8 through 11 are used as an additive in forming an electrode of a fuel cell, hydrophobicity of the electrode may be adjusted, and the oxygen permeability of the electrode may be improved. Thus, even when air is used in a cathode of the fuel cell, activation time may be reduced, and performance of the fuel cell may be improved.

In addition, the compounds of Formulae 8 through 11 have high ductility, and when used as an electrode additive may increase binding force between the electrode including the compounds and a substrate.

The product of polymerization of the above-described composition may be a product of polymerization of at least one selected from among the compound of Formula 1 and the compound of Formula 2, or may be a product of polymerization of at least one selected from among the compound of Formula 1 and the compound of Formula 2, and a cross-linkable compound.

The cross-linkable compound may be any compound having a functional group that is cross-linkable with at least one of the compound of Formula 1 and the compound of Formula 2.

For example, the cross-linkable compound may be any nitrogen-containing aromatic compound. Non-limiting examples of the cross-linkable compound include a five-membered cyclic nitrogen-containing aromatic compound, and a six-membered cyclic nitrogen-containing aromatic compound, for example, polypyrimidine.

The cross-linkable compound may be at least one material selected from the group consisting of a polyazole-based material, polyoxazole and polyimide.

When a polyazole-based material is used as the cross-linkable compound, a final product may be a graft copolymer obtained through graft polymerization of a polymer of at least one selected from among the compound of Formula 1 and the compound of Formula 1, and the polyazole-based material.

As used herein, the term "a product of polymerization of at least one selected from among the compound of Formula 1 and the compound of Formula 2, and a polyazole-based material" may be used to indicate a product of polymerization of at least one of the compounds of Formulae 1 and 2 and a polyazole-based material, or the graft copolymer described above.

The polyazole-based material is a polymer having a repeating unit including at least one aryl ring having at least one nitrogen atom.

The aryl ring may be a 5-membered or 6-membered atom ring fused to another ring, such as another aryl ring or a heteroaryl ring, wherein the 5-membered or 6-membered atom ring includes one to three nitrogen atoms. In this regard, the nitrogen atoms may be substituted with an oxygen, phosphorus and/or sulfur atom. Non-limiting examples of the aryl ring include hexahydroindyl, indanyl, and tetrahydronaphthyl.

The polyazole-based material may have at least one amino group in the repeating unit described above. In this regard, the at least one amino group may be a primary, secondary or tertiary amino group as part of the aryl ring or substituent part of an aryl ring.

The term "amino" includes compounds wherein a nitrogen atom is covalently bonded to at least one carbon or heteroatom. The term "amino" also includes —NH$_2$ and also includes substituted moieties.

The term also includes "alkyl amino" wherein the nitrogen is bound to at least one additional alkyl group. The term also includes "arylamino" and "diarylamino" groups wherein the nitrogen is bound to at least one or two independently selected aryl groups, respectively.

Methods of preparing the polyazole-based material and a polymer film including the polyazole-based material are disclosed in US 2005/256296. The polyazole-based material may include an azole unit represented by one of the following formulae 17-30.

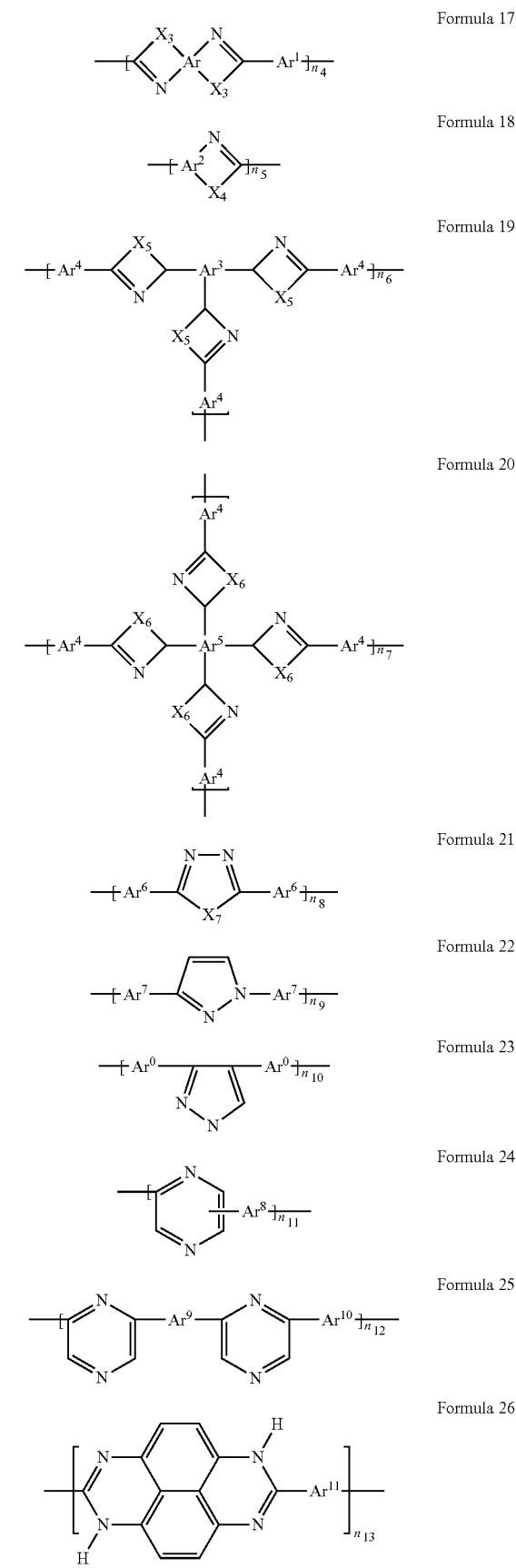

-continued

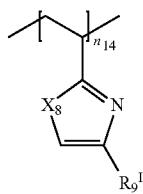

Formula 27

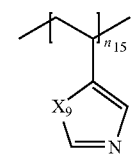

Formula 28

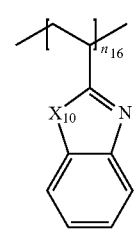

Formula 29

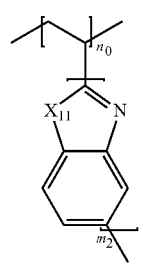

Formula 30

In Formulae 17-30 above, $Ar^0$ may be identical to or different from another $Ar^0$, or any other $Ar^n$ (where n can be no superscript or 1 to 11), and may be a tetravalent monocyclic or polycyclic $C_6$-$C_{20}$ aryl group or $C_2$-$C_{20}$ heteroaryl group;

Ar may be identical to or different from another Ar, or any other $Ar^n$ (where n can be no superscript or 1 to 11), and may be a tetravalent monocyclic or polycyclic $C_6$-$C_{20}$ aryl group or $C_2$-$C_{20}$ heteroaryl group;

$Ar^1$ may be identical to or different from another $Ar^1$, or any other $Ar^n$ (where n can be no superscript or 1 to 11), and may be a bivalent monocyclic or polycyclic $C_6$-$C_{20}$ aryl group or $C_2$-$C_{20}$ heteroaryl group;

$Ar^2$ may be identical to or different from another $Ar^2$, or any other $Ar^n$ (where n can be no superscript or 1 to 11), and may be a bivalent or trivalent monocyclic or polycyclic $C_6$-$C_{20}$ aryl group or $C_2$-$C_{20}$ heteroaryl group;

$Ar^3$ may be identical to or different from another $Ar^3$, or any other $Ar^n$ (where n can be no superscript or 1 to 11), and may be a trivalent monocyclic or polycyclic $C_6$-$C_{20}$ aryl group or $C_2$-$C_{20}$ heteroaryl group;

$Ar^4$ may be identical to or different from another $Ar^4$, or any other $Ar^n$ (where n can be no superscript, 0 or 1 to 11), and may be a trivalent monocyclic or polycyclic $C_6$-$C_{20}$ aryl group or $C_2$-$C_{20}$ heteroaryl group;

$Ar^5$ may be identical to or different from another $Ar^5$, or any other $Ar^n$ (where n can be no superscript, 0 or 1 to 11), and may be a tetravalent monocyclic or polycyclic $C_6$-$C_{20}$ aryl group or $C_2$-$C_{20}$ heteroaryl group;

$Ar^6$ may be identical to or different from another $Ar^6$, or any other $Ar^n$ (where n can be no superscript, 0 or 1 to 11), and may be a bivalent monocyclic or polycyclic $C_6$-$C_{20}$ aryl group or $C_2$-$C_{20}$ heteroaryl group;

$Ar^7$ may be identical to or different from another $Ar^7$, or any other $Ar^n$ (where n can be no superscript, 0 or 1 to 11), and may be a bivalent monocyclic or polycyclic $C_6$-$C_{20}$ aryl group or $C_2$-$C_{20}$ heteroaryl group;

$Ar^8$ may be identical to or different from another $Ar^8$, or any other $Ar^n$ (where n can be no superscript 0 or 1 to 11), and may be a trivalent monocyclic or polycyclic $C_6$-$C_{20}$ aryl group or $C_2$-$C_{20}$ heteroaryl group;

$Ar^9$ may be identical to or different from another $Ar^9$, or any other $Ar^n$ (where n can be no superscript, 0 or 1 to 11), and may be a bivalent, trivalent or tetravalent monocyclic or polycyclic $C_6$-$C_{20}$ aryl group or $C_2$-$C_{20}$ heteroaryl group;

$Ar^{10}$ may be identical to or different from another $Ar^{10}$, or any other $Ar^n$ (where n can be no superscript, 0 or 1 to 11), and may be a bivalent or trivalent monocyclic or polycyclic $C_6$-$C_{20}$ aryl group or $C_2$-$C_{20}$ heteroaryl group;

$Ar^{11}$ may be identical to or different from another $Ar^{11}$, or any other $Ar^n$ (where n can be no superscript, 0 or 1 to 11), and may be a bivalent monocyclic or polycyclic $C_6$-$C_{20}$ aryl group or $C_2$-$C_{20}$ heteroaryl group;

$X_3$ to $X_{11}$ may be identical to or different from each other, and may be an oxygen atom, a sulfur atom or —N(R'); and R' may be a hydrogen atom, a $C_1$-$C_{20}$ alkyl group, a $C_1$-$C_{20}$ alkoxy group, or a $C_6$-$C_{20}$ aryl group;

$R_9'$ may be a hydrogen atom, a $C_1$-$C_{20}$ alkyl group or a $C_6$-$C_{20}$ aryl group; and For the polymer repeating units, $n_0$, $n_4$ to $n_{16}$, and $m_2$ may each be independently an integer of 10 or greater, and in some embodiments, may each be independently an integer of 100 or greater, for example, in the range of 100 to 100,000.

Examples of the aryl or heteroaryl group include benzene, naphthalene, biphenyl, diphenylether, diphenylmethane, diphenyldimethylmethane, bisphenone, diphenylsulfone, quinoline, pyridine, bipyridine, pyridazine, pyrimidine, pyrazine, triazine, tetrazine, pyrrole, pyrazole, anthracene, benzopyrrole, benzotriazole, benzoxathiazole, benzoxadiazole, benzopyridine, benzopyrazine, benzopyrazidine, benzopyrimidine, benzotriazine, indolizine, quinolizine, pyridopyridine, imidazopyrimidine, pyrazinopyrimidine, carbazole, aziridine, phenazine, benzoquinoline, phenoxazine, phenothiazine, acridizine, benzopteridine, phenanthroline and phenanthrene, wherein these aryl or heteroaryl groups may have a substituent.

Ar, $Ar^0$, $Ar^1$, $Ar^4$, $Ar^6$, $Ar^7$, $Ar^8$, $Ar^9$, $Ar^{10}$, and $Ar^{11}$ defined above may have any substitutable pattern. For example, if the aryl or heteroaryl group is phenylene, Ar, $Ar^0$, $Ar^1$, $Ar^4$, $Ar^6$, $Ar^7$, $Ar^8$, $Ar^9$, $Ar^{10}$ and $Ar^{11}$ may be ortho-phenylene, meta-phenylene or para-phenylene.

The alkyl group may be a $C_1$-$C_4$ short-chain alkyl group, such as methyl, ethyl, n-propyl, i-propyl or t-butyl. The aryl group may be, for example, a phenyl group or a naphthyl group.

Examples of the substituent include a halogen atom, such as fluorine, an amino group, a hydroxyl group, and a short-chain alkyl group, such as methyl or ethyl.

Examples of the polyazole-based material include polyimidazole, polybenzothiazole, polybenzoxazole, polyoxadiazole, polyquinoxaline, polythiadiazole, polypyridine, polypyrimidine, and polytetrazapyrene.

The polyazole-based material may be a copolymer or blend including at least two units selected from the group consisting of units represented by Formulae 1 through 14 above. The polyazole-based material may be a block copolymer (di-block or tri-block), a random copolymer, a periodic copolymer or an alternating polymer including at least two units selected from the units of Formulae 1 through 14.

For example, a polyazole-based material including at least one of the units of Formulae 17 and 18 may be used.
Examples of the polyazole-based material include polymers are also represented by the following Formulae 31-57:
Formula 31
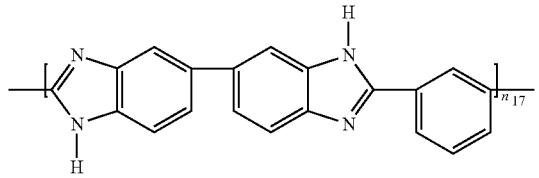
Formula 32
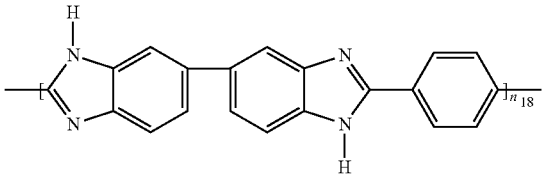
Formula 33
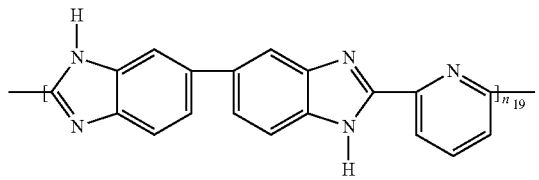
Formula 34
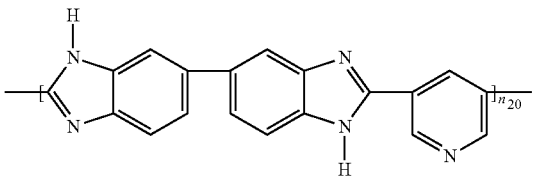
Formula 35
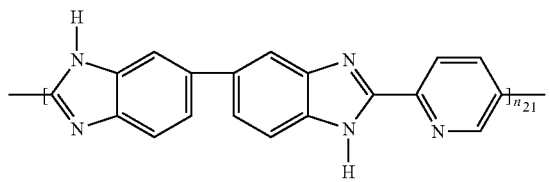
Formula 36
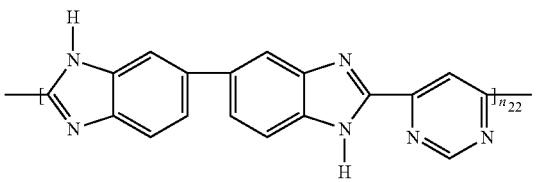
Formula 37
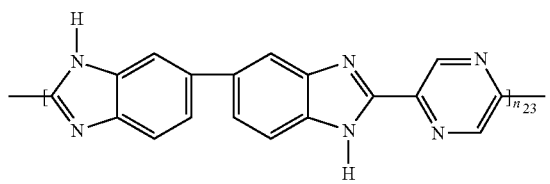
Formula 38
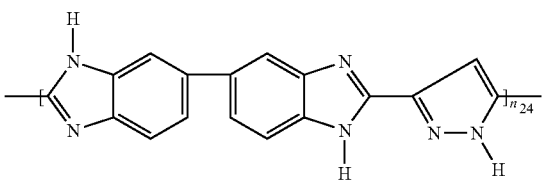
Formula 39
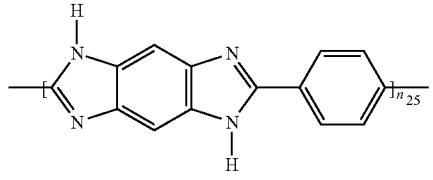
Formula 40
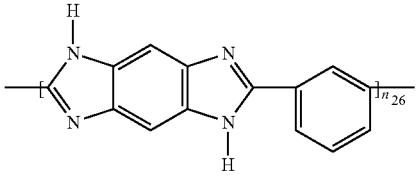
Formula 41
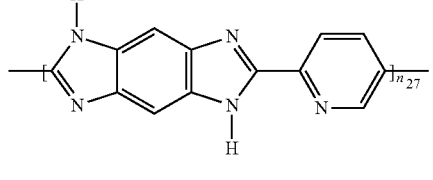
Formula 42
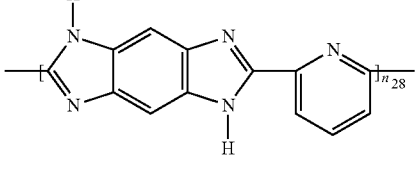
Formula 43
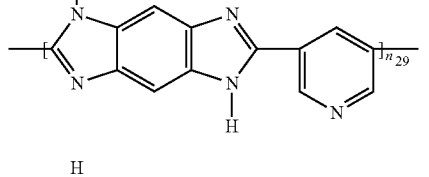
Formula 44
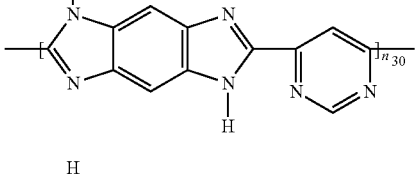
Formula 45
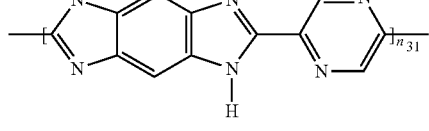
Formula 46
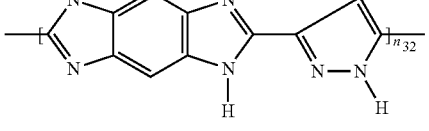

-continued

Formula 47
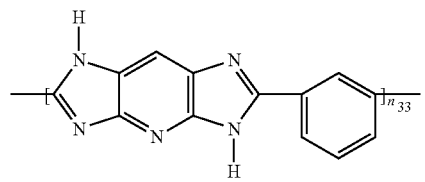

Formula 48
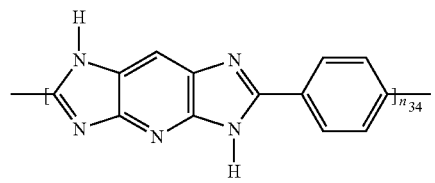

Formula 49
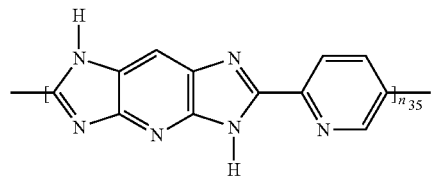

Formula 50
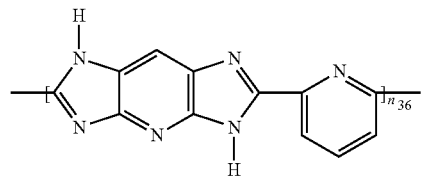

Formula 51
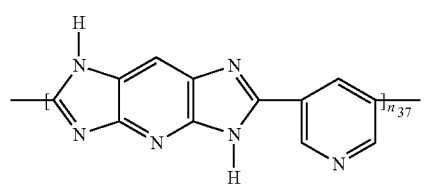

Formula 52
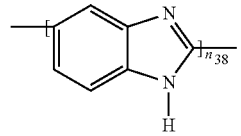

Formula 53
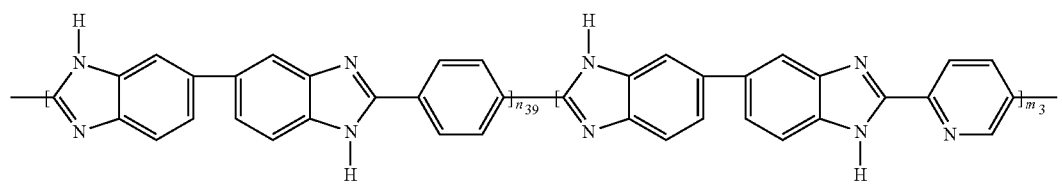

Formula 54
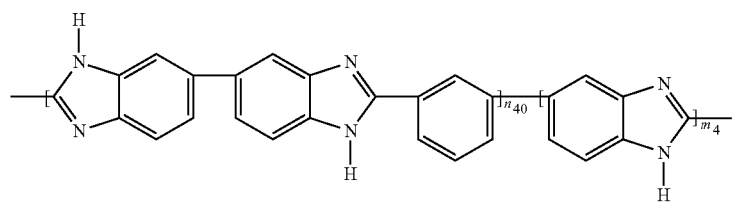

Formula 55
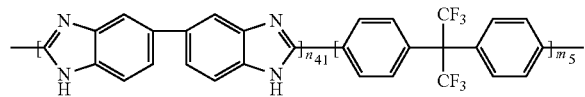

Formula 56
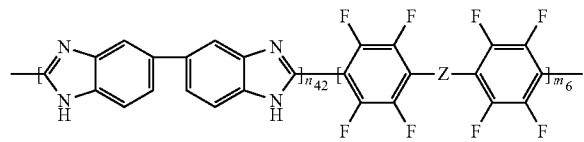

Formula 57
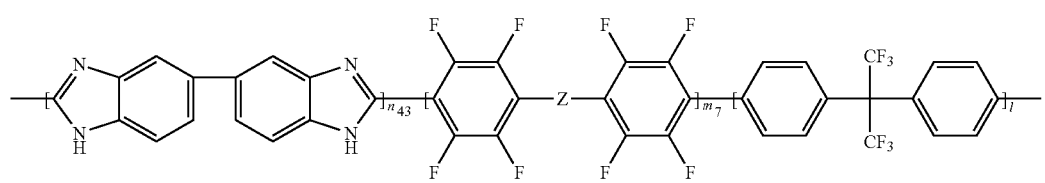

In Formulae 31-57 above, l, $n_{17}$ to $n_{43}$, and $m_3$ to $m_7$ may be each independently an integer of 10 or greater, and in some embodiments, may be each independently an integer of 100 or greater; and z may be a chemical bond, —$(CH_2)_s$—, —C(=O)—, —$SO_2$—, —$C(CH_3)_2$—, or —$C(CF_3)_2$— where s may be an integer from 1 to 5.

The polyazole-based material may be a compound (m-polybenzimidazole or m-PBI) represented by Formula 12 below, or compound (p-PBI) represented by Formula 13 below.

Formula 12
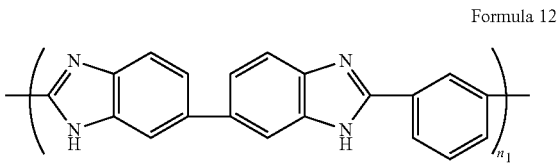

In Formula 12, $n_1$ is an integer of 10 or greater.

Formula 13

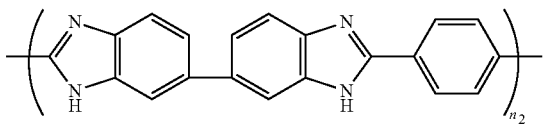

In Formula 13, $n_2$ is an integer of 10 or greater, and in some embodiments, may be an integer of 100 or greater. These polymeric compounds may have a number average molecular weight of 1,000,000 or less.

For example, the polyazole-based material may be a polymer represented by Formula 14 below.

Formula 14

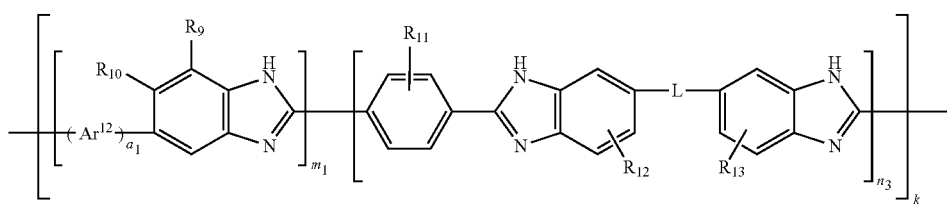

In Formula 14, $R_9$ and $R_{10}$ are each independently a hydrogen atom, an unsubstituted or substituted $C_1$-C alkyl group, a unsubstituted or substituted $C_1$-$C_{20}$ alkoxy group, a unsubstituted or substituted $C_6$-$C_{20}$ aryl group, a unsubstituted or substituted $C_6$-$C_{20}$ aryloxy group, a unsubstituted or substituted $C_3$-$C_{20}$ heteroaryl group, or a unsubstituted or substituted $C_3$-$C_{20}$ heteroaryloxy group, or $R_9$ and $R_{10}$ may be linked to form a $C_4$-$C_{20}$ carbocyclic or a $C_3$-$C_{20}$ hetero ring, $Ar^{12}$ is a substituted or unsubstituted $C_6$-$C_{20}$ aryl group or a substituted or unsubstituted $C_3$-$C_{20}$ heteroaryl group;

$R_{11}$ to $R_{13}$ are each independently a mono- or a multi-substituted substituent selected from the group consisting of a hydrogen atom, an unsubstituted or substituted $C_1$-$C_{20}$ alkyl group, an unsubstituted or substituted $C_1$-$C_{20}$ alkoxy group, an unsubstituted or substituted $C_6$-$C_{20}$ aryl group, an unsubstituted or substituted $C_6$-$C_{20}$ aryloxy group, an unsubstituted or substituted $C_3$-$C_{20}$ heteroaryl group, or an unsubstituted or substituted $C_3$-$C_{20}$ heteroaryloxy group, or $R_1$ and $R_2$ may be linked to form a $C_4$-$C_{20}$ carbocyclic or a $C_3$-$C_{20}$ hetero ring;

L represents a linker;

$m_1$ is a number from 0.01 to 1;

$a_1$ is 0 or 1;

$n_3$ is a number from 0 to 0.99; and k is a number from 10 to 250.

The polymer may be a compound represented by Formula 15 below or a compound represented by Formula 16 below:

Formula 15

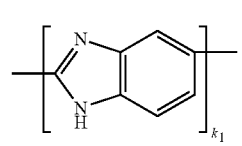

In Formula 15, $k_1$ represents a degree of polymerization and is a number from 10 to 300.

Formula 16

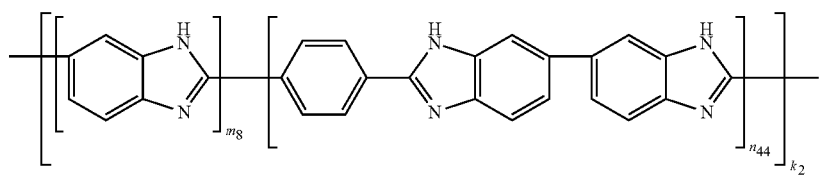

In Formula 16, $m_8$ is a number from 0.01 to 1, for example, 1 or a number from 0.1 to 0.9; and $n_{44}$ is a number from 0 to 0.99, for example, 0 or a number from 0.1 to 0.9; and $k_2$ is a number from 10 to 250.

When at least one selected from among the compound of Formula 1 and the compound of Formula 2 is polymerized with the polyazole-based material, the amount of the cross-linkable compound may be in the range of about 5 to about 210 parts by weight, and in some embodiments, may be about 40 to about 210 parts by weight, based on 100 parts by weight of at least one from among the compound of Formula 1 and the compound of Formula 2. When the amount of the cross-linkable compound is within these ranges, proton conductivity may be good.

Hereinafter, as a process involved in the preparation of the polymer, a method of preparing a compound represented by Formula 4 below, according to an exemplary embodiment of the present invention, will be described.

The compound of Formula 4 may be prepared through reaction of a phenol compound (A), formaldehyde (B) and an amine compound (C), as illustrated in Reaction Scheme 1 below. The reaction conditions are not particularly limited. For example, the reaction may be performed using a melt process in the absence of a solvent. The reaction temperature may be from about 80 to 100° C., but may be varied according to the particular substituents used.

Reaction Scheme 1

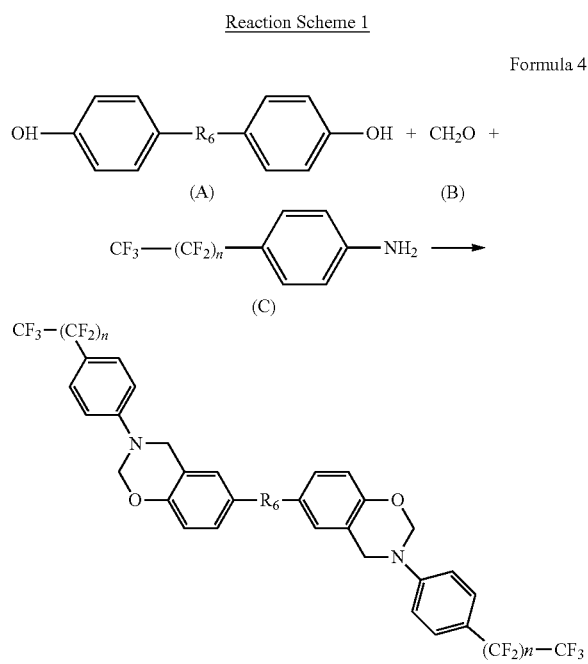

In the compounds (A), (B), and (C), and Formula 4 above in Reaction Scheme 1, n may be an integer from 1 to 20; and $R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(=O)—, —O—, and —SO$_2$—.

The compound of Formula 1 may be synthesized in a similar manner as the compound of Formula 4, which is an example of the compound of Formula 2.

The composition and/or the polymer thereof may be used as an electrode additive for fuel cells. When the composition and/or the polymer thereof are used as an electrode additive, the electrode of a fuel cell may include a catalyst, in addition to the composition and/or the polymer thereof.

At least one compound selected from the group consisting of the compound of Formula 1, the compound of Formula 2; and polymers of these compounds may improve the wettability of the electrode with phosphoric acid. The amount thereof may be from about 0.001 to 0.5 parts by weight, based on 1 part by weight of the catalyst.

When the amount of at least one compound selected from among the compound of Formula 1 and the compound of Formula 2 is within this range, oxygen permeability and oxygen solubility characteristics of the electrode may be improved.

The catalyst for the electrode may be platinum (Pt), an alloy or a mixture of platinum (Pt) and at least one metal selected from the group consisting of gold (Au), palladium (Pd), rhodium (Ru), iridium (Ir), ruthenium (Ru), tin (Sn), molybdenum (Mo), cobalt (Co), and chromium (Cr). The Pt, the alloy, or the mixture may be supported on a carbonaceous support.

The electrode may further include a binder.

The binder may be at least one selected from the group consisting of poly(vinylidenefluoride), polytetrafluoroethylene (PTFE), a tetrafluoroethylene-hexafluoropropylene copolymer, perfluoroethylene, and polyurethane.

The amount of the binder may be in the range of about 0.001 parts to about 0.5 parts by weight, based on 1 part by weight of the catalyst. When the amount of the binder is within this range, the wettability of the electrode may be improved.

The electrode for a fuel cell described above may be manufactured using any known method. For example, the electrode may be manufactured using a method described below.

First, a catalyst is dispersed in a solvent to obtain a dispersion solution. The solvent may be N-methylpyrrolidone (NMP), dimethylacetamide (DMAc), or the like. The amount of the solvent may be in the rage of about 1 to about 10 parts by weight, based on 1 part by weight of the catalyst.

A mixture containing a solvent and at least one of the compound of Formula 1 and the compound of Formula 2 is added to the dispersion solution and stirred to obtain a coating solution. A binder may be further added to the coating solution. Alternatively, a polyazole-based material may be further added to the coating solution.

The solvent may be N-methylpyrrolidone (NMP), dimethylacetamide (DMAc), or the like. The amount of at least one of the compound of Formula 1 and the compound of Formula 2 may be in the range of about 0.001 to 0.5 parts by weight based on 1 part by weight of the catalyst. The amount of the binder may be in the range of about 0.001 to about 0.5 parts by weight based on 1 part by weight of the catalyst.

The coating solution is coated on a surface of a support and then dried, thereby completing the manufacture of the electrode.

Examples of the support include a carbon support, a support substrate such as a polyethylene terephthalate (PET) film or a MYLAR® film (DuPont Company trademark for biaxially-oriented PET or boPET), and the like.

When a carbon support is used as the support, the carbon support may be fixed on a glass substrate to facilitate the coating.

When a support substrate such as a polyethylene terephthalate film or a MYLAR film is used as the support, the electrode may be manufactured by coating the support substrate with the coating solution to form an electrode catalyst layer, separating the electrode catalyst layer from the support substrate, and stacking a carbon support on the electrode catalyst layer.

The method of coating the coating solution is not particularly limited. Examples of the coating method include coating using a doctor blade, bar coating, screen printing, and the like.

After coating the coating solution on the surface of the support, the resulting structure is dried at a temperature of from about 20 to 150° C. to remove the solvent. The drying time may vary according to the drying temperature, and may be in the range of about 10 to about 60 minutes.

A method of manufacturing a fuel cell including the electrode described above will be described below.

Any electrolyte membrane that is commonly used in fuel cells may be used. For example, a polybenzimidazole electrolyte membrane, a polybenzoxazine-polybenzimidazole copolymer electrolyte membrane, a porous polytetrafluoroethylene (PTFE) membrane, or the like may be used. In a similar way to the electrolyte, an electrolyte membrane including a polymerization product of at least one of the compound of Formula 1 and the compound of Formula 2 may be used.

The electrolyte membrane may further be impregnated with a proton conductor.

Examples of the proton conductor include polyphosphoric acid $(H)_{n+2}(P)_n(O)_{3n+1}$, phosphonic acid $(H_3PO_3)$, orthophosphoric acid $(H_3PO_4)$, pyrophosphoric acid $(H_4P_2O_7)$, triphosphoric acid $(H_5P_3O_{10})$, metaphosphoric acid $(HPO_3)$, and a derivative thereof. For example, the proton conductor may be a $C_1$-$C_{20}$ organic phosphonic acid.

The amount of the proton conductor may be at least 80 wt %, for example, 80 wt %, 90 wt %, 95 wt %, or 98 wt %.

The electrolyte membrane may be prepared using a polymerization product of at least one of the compound of Formula 1 and the compound of Formula 2 according to a method disclosed in the U.S. Patent Application Publication US2009/0117436.

The electrolyte membrane may be prepared using, for example, at least one of the compounds represented by the following Formulae 58-60.

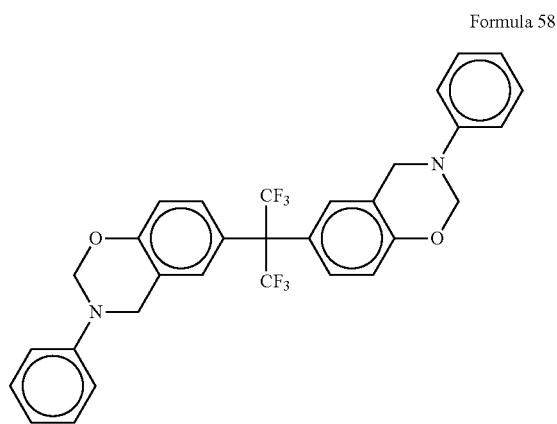

Formula 58

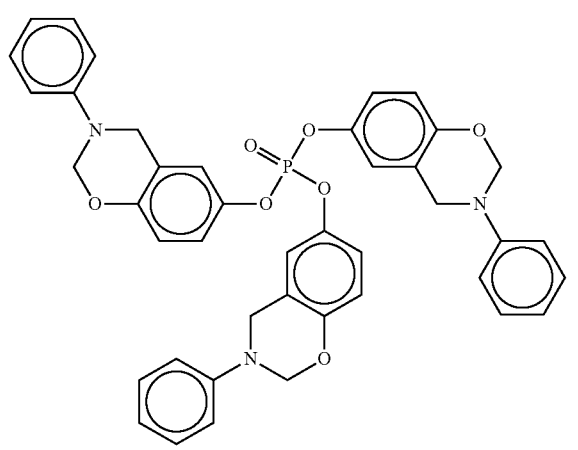

Formula 59

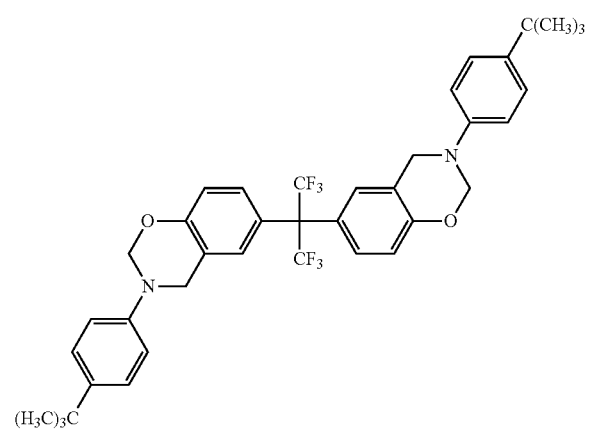

Formula 60

Substituents in the formulae above may be defined as follows.

As used herein, the term "alkyl" refers to a fully saturated branched or unbranched (or straight chain or linear) hydrocarbon moiety.

Examples of the alkyl group used herein include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, and n-heptyl.

At least one hydrogen atom of the alkyl group may be substituted with a halogen atom, a $C_1$-$C_{20}$ alkyl group substituted with a halogen atom (for example, $CCF_3$, $CHCF_2$, $CH_2F$ and $CCl_3$), a $C_1$-$C_{20}$ alkoxy, a $C_2$-$C_{20}$ alkoxyalkyl, a hydroxy group, a nitro group, a cyano group, an amino group, an amidino group, a hydrazine, a hydrazone, a carboxyl group or a salt thereof, a sulfonyl group, a sulfamoyl, a sulfonic acid group or a salt thereof, a phosphoric acid or a salt thereof, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroarylalkyl group, a $C_6$-$C_{20}$ heteroaryloxy group, a $C_6$-$C_{20}$ heteroaryloxyalkyl group, or a $C_6$-$C_{20}$ heteroarylalkyl group.

As used herein, the term "halogen atom" refers to fluoro, bromo, chloro, or iodo.

As used herein, the term "a $C_1$-$C_{20}$ alkyl group substituted with a halogen atom" refers to a $C_1$-$C_{20}$ alkyl group that is substituted with one or more halo groups, and unlimited examples of a $C_1$-$C_{20}$ alkyl group that is substituted with one or more halo groups are monohaloalkyl, dihaloalkyl, and polyhaloalkyl including perhaloalkyl.

A monohaloalkyl has one iodo, bromo, chloro or fluoro within the alkyl group, and dihaloalkyl and polyhaloalkyl groups have two or more of the same halo atoms or a combination of different halo groups within the alkyl.

As used herein, the term "alkoxy" refers to alkyl-O—, wherein alkyl is defined herein above. Examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. At least one hydrogen atom of the alkoxy group may be substituted with the same substituent as described above in connection with the alkyl group.

The term alkoxyalkyl refers to an alkyl group, as defined above, in which the alkyl group is substituted with alkoxy. At least one hydrogen atom of the alkoxyalkyl group may be substituted with the same substituent as described above in connection with the alkyl group. The term alkoxyalkyl includes a substituted alkoxyalkyl moiety.

The term "alkenyl" refers to a branched or unbranched hydrocarbon having at least one carbon-carbon double bond. Examples of alkenyl are, but are not limited to, vinyl, allyl, butenyl, isopropenyl or isobutenyl. At least one hydrogen atom of the alkenyl group may be substituted with the same substituent as described above in connection with the alkyl group.

The term "alkynyl" refers to a branched or unbranched hydrocarbon having at least one carbon-carbon triple bond. Examples of alkynyl are, but are not limited to, ethynyl, butynyl, isobutynyl or isopropynyl.

At least one hydrogen atom of alkynyl may be substituted with the same substituent as described above in connection with the alkyl group.

The term "aryl" is used alone or in combination, and refers to an aromatic hydrocarbon group having one or more rings.

The term "aryl" also refers to a group in which an aromatic ring is fused to one or more cycloalkyl rings.

Examples of aryl are, but are not limited to, phenyl, naphthyl, or tetrahydronaphthyl.

At least one hydrogen atom of aryl may be substituted with the same substituent as described above in connection with the alkyl group.

The term "arylalkyl" is an alkyl substituted with aryl. Examples of arylalkyl are benzyl- or Phenyl-$CH_2CH_2$—.

The term "aryloxy" includes an —O-aryl, wherein aryl is defined herein. Examples of aryloxy are phenoxy and the like. At least one hydrogen atom of aryloxy may be substituted with the same substituent as described above in connection with the alkyl group.

The term "heteroaryl" refers to a monocyclic or bicyclic organic compound that contains one or more hetero atoms selected from N, O, P, and S, and the remaining ring atoms are carton atoms. The heteroaryl may include, for example, 1 to 5 hetero atoms, and 5 to 10 ring members.

S or N may be oxidized to various oxidation states.

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-triazol-3-yl, 1,2,4-triazol-5-yl, 1,2,3-triazol-4-yl, 1,2,3-trizol-5-yl, pyrid-2-yl, pyrid-3-yl, 2-pyrazin-2yl, pyrazin-4-yl, pyrazin-5-yl, 2-pyrimidin-2-yl, 4-pyrimidin-2-yl, and 5-pyrimidin-2-yl.

The term "heteroaryl" also refer to a group in which a heteroaromatic ring is fused to one or more aryl, cycloaliphatic, or heterocyclic rings Examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

At least one hydrogen atom in the heteroaryl group may be substituted with the same substituent as described above in connection with the alkyl group.

The term "heteroarylakyl" refers to alkyl substituted with heteroaryl.

The term "heteroaryloxy" includes an —O-heteroaryl moiety. At least one hydrogen atom in heteroaryloxy may be substituted with the same substituent as described above in connection with the alkyl group.

The term "hetearyloxyalkyl" refers to an alkyl group that is substituted with heteroaryloxy. At least one hydrogen atom in hetearyloxyalkyl may be substituted with the same substituent as described above in connection with the alkyl group.

As used herein, the term "carbocyclic" refers to saturated or partially unsaturated but non-aromatic monocyclic, bicyclic or tricyclic hydrocarbon groups.

Exemplary monocyclic hydrocarbon groups include cyclopentyl, cyclopentenyl, cyclohexyl and cyclohexenyl.

Exemplary bicyclic hydrocarbon groups include bornyl, decahydronaphthyl, bicyclo[2.1.1]hexyl, bicyclo[2.2.1]heptyl, bicyclo[2.2.1]heptenyl, and bicyclo[2.2.2]octyl.

Exemplary tricyclic hydrocarbon groups include adamantyl.

At least one hydrogen atom in carbocyclic may be substituted with the same substituent as described above in connection with the alkyl group.

The term "heterocyclic" refers to a ring containing 5-10 ring atoms including a hetero atom such as N, S, P, or O, and an example of heterocyclic is pyridyl. At least one hydrogen atom in heterocyclic may be substituted with the same substituent as described above in connection with the alkyl group.

The term "heterocyclicoxy" includes an —O-heterocyclic, and at least one hydrogen atom in heterocyclicoxy may be substituted with the same substituent as described above in connection with the alkyl group.

The term "sulfonyl" includes R"—$SO_2$—, wherein R" is hydrogen, alkyl, aryl, heteroaryl, aryl-alkyl, heteroaryl-alkyl, alkoxy, aryloxy, cycloalkyl, or heterocyclic.

The term "sulfamoyl" includes $H_2NS(O)_2$—, alkyl-NHS$(O)_2$—, (alkyl)2NS$(O)_2$—, aryl-NHS$(O)_2$—, alkyl(aryl)-NS$(O)_2$—, (aryl)2NS(O)2-, heteroaryl-NHS(O)2-, (aryl-alkyl)-, NHS$(O)_2$—, or (heteroaryl-alkyl)-NHS$(O)_2$—.

At least one hydrogen atom in sulfamoyl may be substituted with the same substituent as described above in connection with the alkyl group.

The term "amino" includes compounds wherein a nitrogen atom is covalently bonded to at least one carbon or heteroatom. The term "amino" also includes —$NH_2$ and also includes substituted moieties.

The term also includes "alkyl amino" wherein the nitrogen is bound to at least one additional alkyl group. The term also includes "arylamino" and "diarylamino" groups wherein the nitrogen is bound to at least one or two independently selected aryl groups, respectively.

The term "alkylene", "alkenylene", "alkynylene", "arylene", and "heteroarylene" are defined as described above, except that "alkyl", "alkenyl", "alkynyl", "aryl", and "heteroaryl", which are mono-valent groups, are changed into divalent groups.

At least one hydrogen atom in "alkylene", "alkenylene", "alkynylene", "arylene", and "heteroarylene" may be substituted with the same substituent as described above in connection with the alkyl group.

In the fuel cell described above, its electrode has a reduced activation time and improved cell voltage characteristics with respect to current density, and its electrolyte membrane has excellent thermal stability at high temperatures and improved acid retention ability. The fuel cell is suitable for use in high-temperature, non-humidified conditions.

Hereinafter, one or more embodiments of the present invention will be described in detail with reference to the following examples. These examples are not intended to limit the purpose and scope of the one or more embodiments of the present invention.

Synthesis Example 1

Preparation of Compound of Formula 8

The structure of the obtained compound of Formula 8 was identified using nuclear magnetic resonance (NMR) spectrometry.

Figure 2:
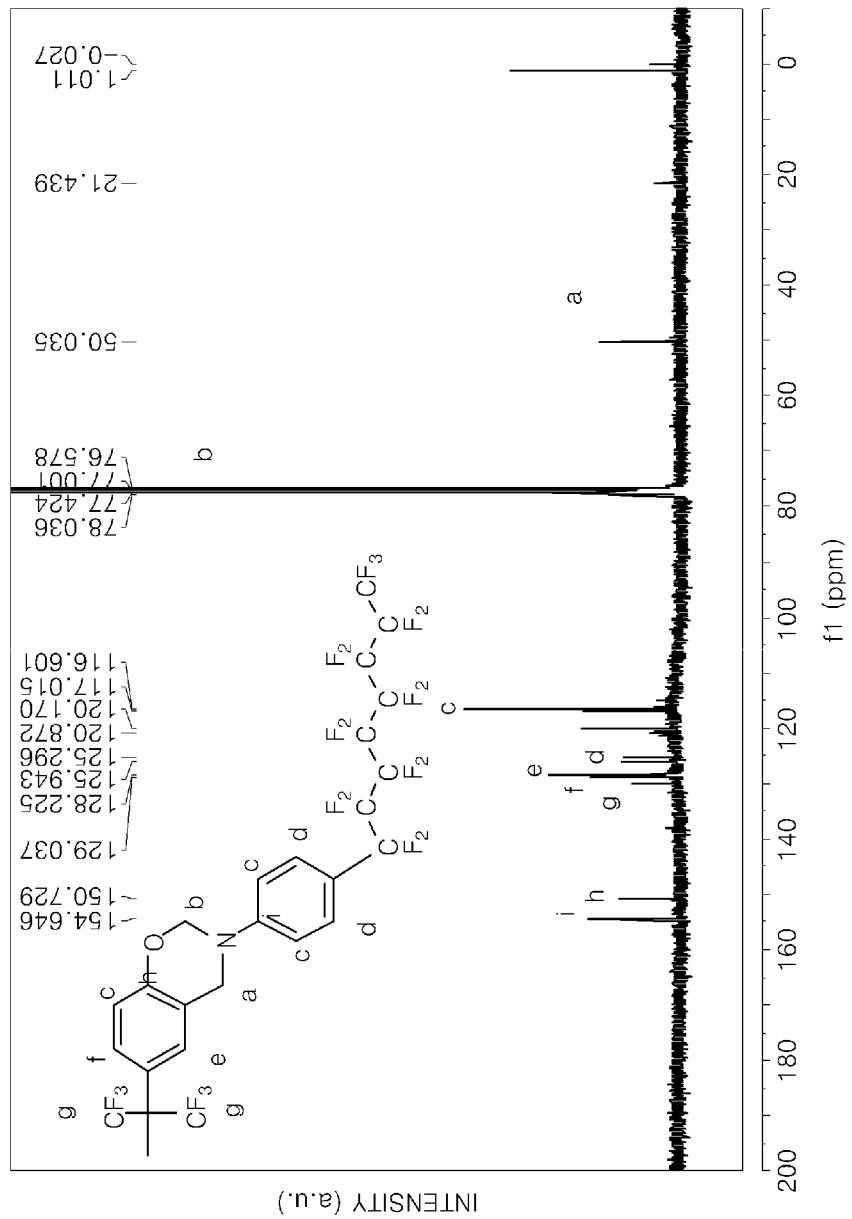
Figure 3:
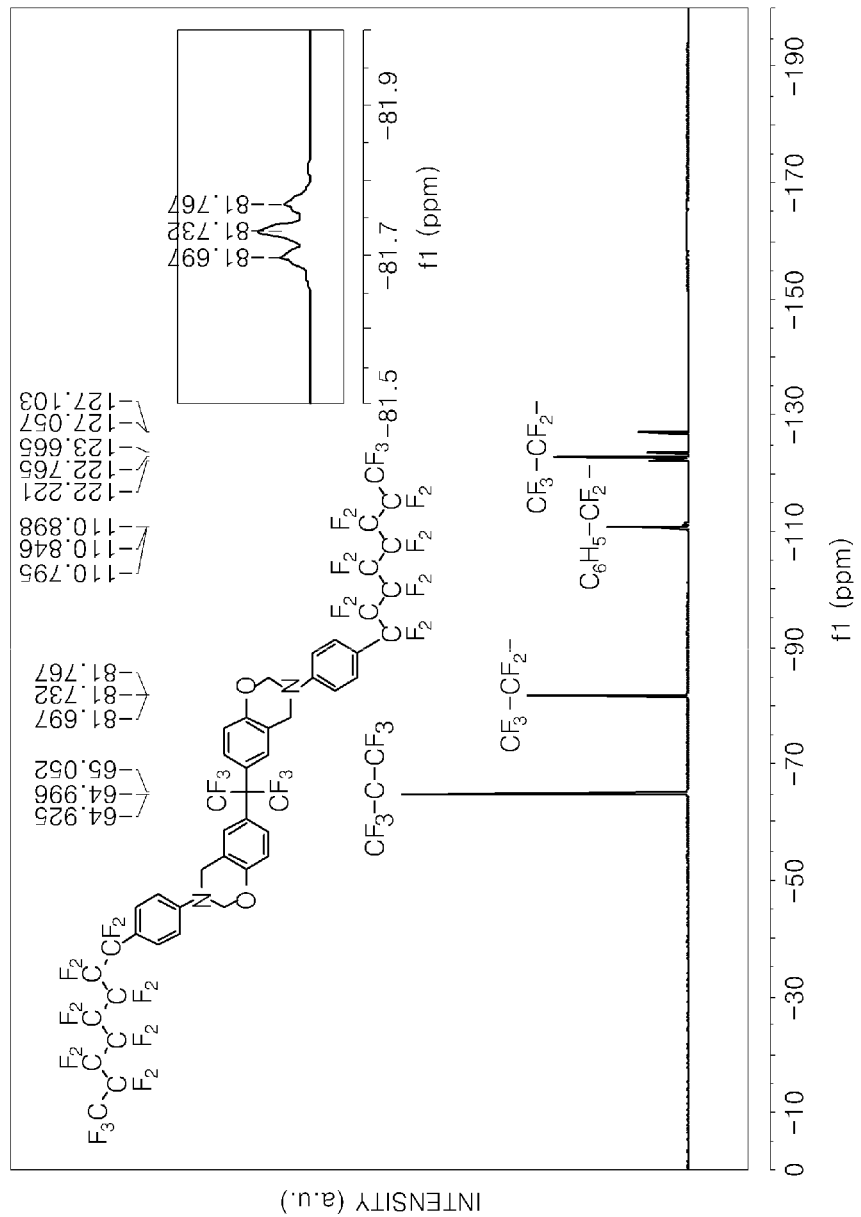

The structure of the compound of Formula 8 was identified from FIGS. 1 through 3. FIGS. 1, 2 and 3 are a 1H-nuclear magnetic resonance (1H-NMR) spectrum, 13C-NMR spectrum, and 19F-NMR spectrum of the compound of Formula 8, respectively.

Thermal characteristics of the compound of Formula 8 were measured by thermogravimetric analysis (TGA). The results are shown in FIG. 4.

Figure 4:
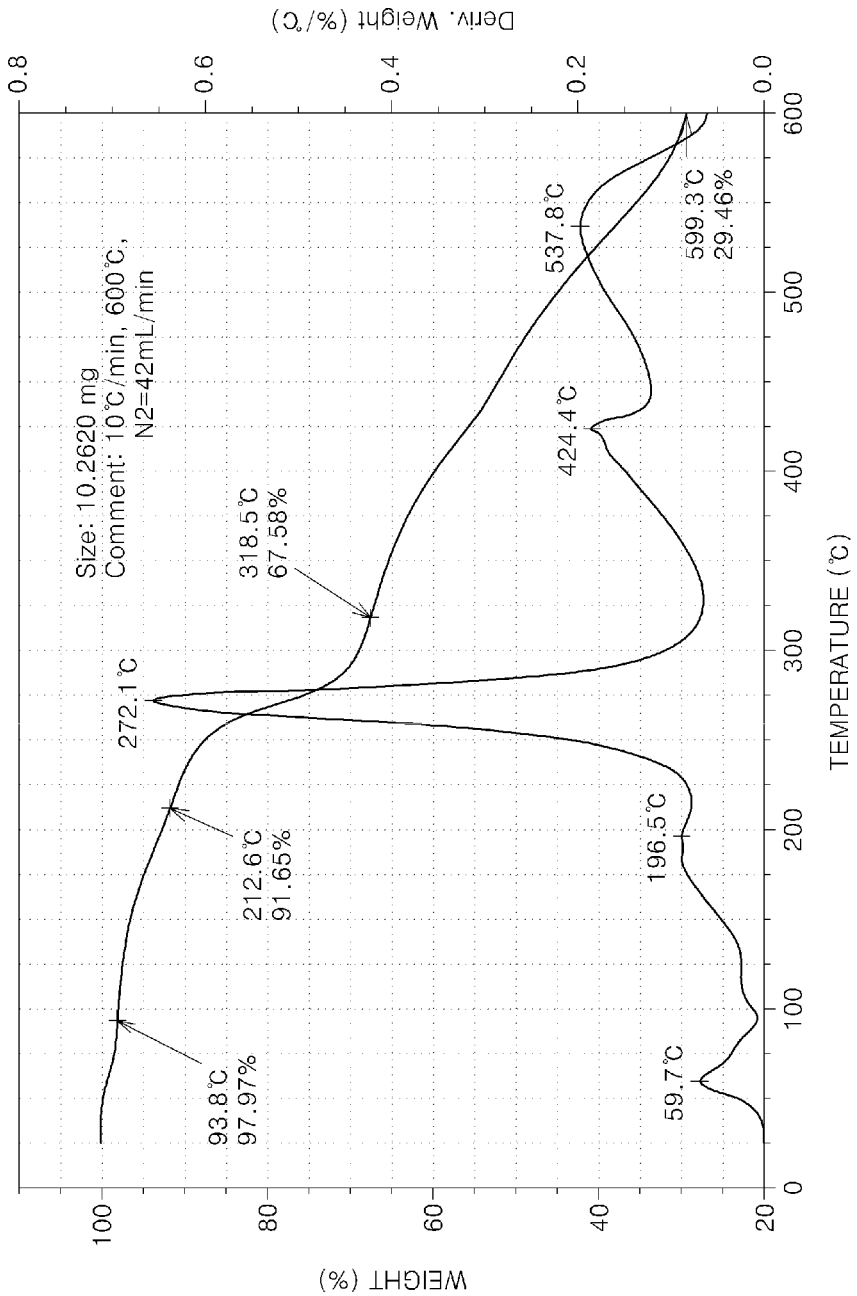
FIG. 4 is a graph illustrating results of thermogravimetric analysis (TGA) on the compound of Formula 8 prepared in Synthesis Example 1.

Referring to FIG. 4, the compound of Formula 8 was found to be thermally stable in an operating temperature range of a fuel cell.

Synthesis Example 2

Preparation of Compound of Formula 9

A compound of Formula 9 was prepared in the same manner as in Synthesis Example 1, except that 3-(heptadecafluo-

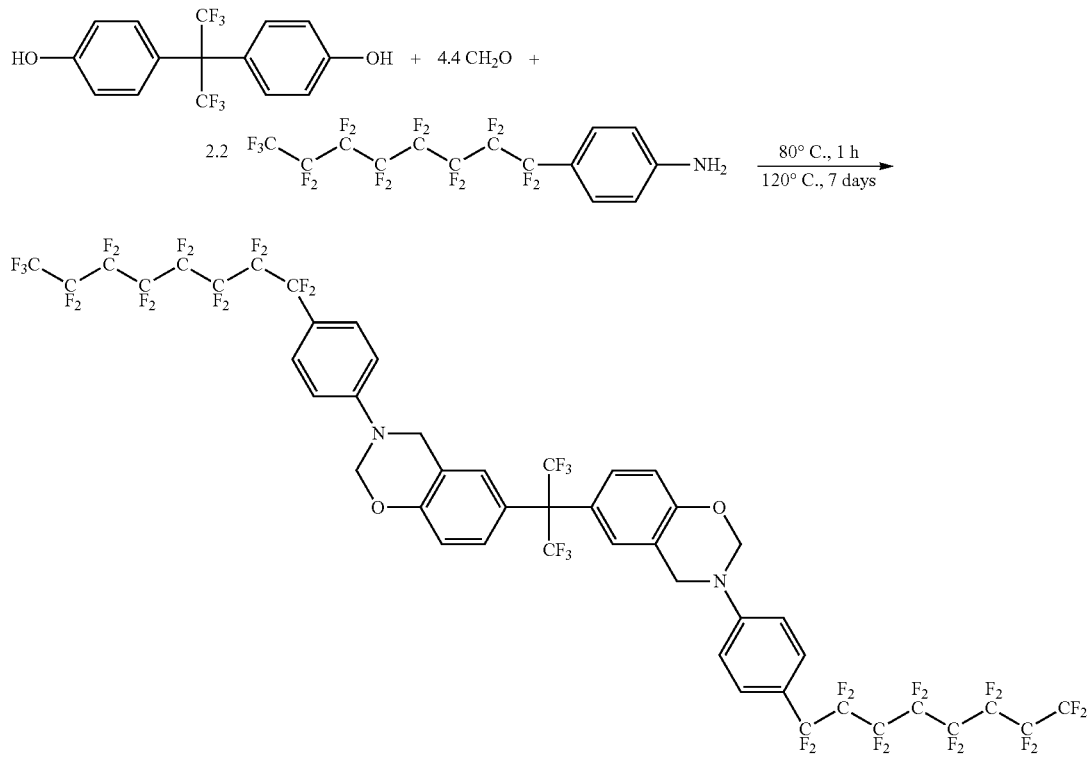

1 mol of 4,4'-hexafluoroisopropylidene diphenol (4,4'-HFIDPH), 4.4 mol of formaldehyde and 2.2 mol of 4-(heptadecafluorooctyl)aniline were mixed together, and the mixture was stirred at 100° C. for 1 hour without a solvent to obtain a crude product.

The crude product was washed twice with 1N NaOH aqueous solution and once with distilled water, and dried with magnesium sulfate. Subsequently, the resultant was filtered and then the solvent was removed therefrom. Then, the resultant was dried in a vacuum to obtain the benzoxazine-based monomer of Formula 8 with a yield of 96%.

rooctyl)aniline was used instead of 4-(heptadecafluorooctyl) aniline.

Synthesis Example 3

Preparation of compound of Formula 10

A compound of Formula 10 was prepared in the same manner as in Synthesis Example 1, except that 2-(heptadecafluorooctyl)aniline was used instead of 4-(heptadecafluorooctyl)aniline.

Synthesis Example 4

Preparation of Compound of Formula 11

A compound of Formula 11 was prepared in the same manner as in Synthesis Example 1, except that 2,4,6-(heptadecafluorooctyl)aniline was used instead of 4-(heptadecafluorooctyl)aniline.

Example 1

Manufacture of Electrodes for Fuel Cells and a Fuel Cell Including the Electrodes 1 g of a catalyst including 50% by weight of Pt/Co loaded on carbon, and 3 g of N-methylpyrrolidone (NMP) as a solvent were added to a stirring vessel, and the mixture was agitated using a mortar to prepare a slurry. A 10 wt % solution of the compound of Formula 8 in NMP was added to the slurry until the slurry contained 0.026 g of the compound of Formula 8, followed by agitating.

Next, a solution of 5 wt % of a vinylidenefluoride-co-hexafluoropropylene copolymer in NMP was added to the mixture until the amount of the vinylidenefluoride-co-hexafluoropropylene copolymer in the mixture reached 0.026 g, followed by mixing for 10 minutes, to prepare a slurry for forming a cathode catalyst layer.

Carbon paper was cut to a size of 4×7 cm², fixed on a glass plate, and coated with the slurry by using a doctor blade (Sheen Instruments Ltd) having a gap of about 600 μm.

The slurry for forming a cathode catalyst layer was coated on the carbon paper, and the resultant was dried at room temperature for 1 hour, dried at 80° C. for 1 hour, dried at 120° C. for 30 minutes, and dried at 150° C. for 15 minutes to manufacture a cathode. The loading amount of Pt of Pt/Co in the cathode was 0.9 mg/cm2.

Anodes were manufactured as follows.

2 g of a Pt catalyst (50 wt % of Pt supported on carbon) and 9 g of N-methylpyrrolidone (NMP) as a solvent were put into a stirring vessel, and stirred using a high-speed stirrer for two minutes. Then, a solution of 0.05 g of polyvinylidenefluoride in 1 g of NMP was added to the reaction solution, followed by stirring for two minutes, to prepare a slurry for forming an anode catalyst layer. The slurry was coated on carbon paper, which was coated with a microporous layer, using a bar coater, to complete the manufacture of the anode. The loading amount of platinum in the anode was 1.522 mg/cm2.

Meanwhile, 65 parts by weight of a compound (HF-a) represented by Formula 58 below and 35 parts by weight of polybenzimidazole (m-PBI) of Formula 12 were blended, and the blend was cured at a temperature of about 80 to about 220° C.

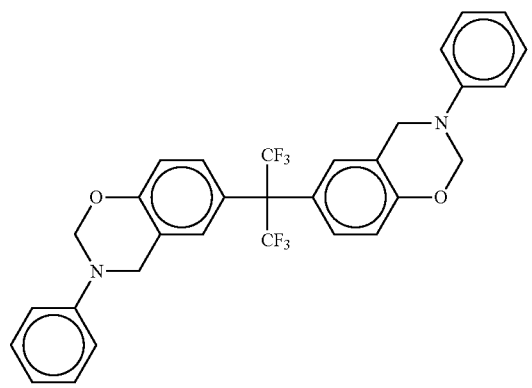

Formula 58

HF-a

Subsequently, the resultant was impregnated with 85 wt % of phosphoric acid at 80° C. for 4 hours or longer to form an electrolyte membrane. Herein, the amount of phosphoric acid was about 500 parts by weight, based on 100 parts by weight of the electrolyte membrane.

The electrolyte membrane was disposed between the cathode and the anode to manufacture a membrane-electrode assembly (MEA). The cathode and the anode were not impregnated with phosphoric acid.

To prevent gas permeation between the cathode and the anode, a PTFE membrane main-gasket having a thickness of 200 μm and a PTFE membrane sub-gasket having a thickness of 20 μm were joined and disposed between each of the anode and cathode, and the electrolyte membrane. The pressure applied to the MEAs was adjusted using a torque wrench, and was stepwise increased using 1, 2, and 3 N-m Torque wrenches.

Electricity was generated by supplying hydrogen to the anode (flow rate: 100 ccm) and air to the cathode (flow rate: 250 ccm), at 150° C., without humidifying the electrolyte membrane, and characteristics of the fuel cell were measured. Herein, since an electrolyte doped with phosphoric acid was used, the performance of the fuel cell improved as time went by. Thus, the fuel cell was activated until the operating voltage reached a peak voltage, and then the characteristics of the fuel cell were evaluated. The area of each of the cathode and the anode was set to 2.8×2.8=7.84 cm². The cathode was about 430 μm thick and the anode was about 390 μm thick.

Examples 2-4

Manufacture of Electrodes for Fuel Cells and a Fuel Cell Including the Electrodes Fuel cells were manufactured in the same manner as in Example 1, except that the compounds of Formulae 9, 10 and 11 were respectively used, instead of the compound of Formula 8.

Comparative Example 1

Manufacture of Electrodes for Fuel Cells and a Fuel Cell Including the Electrodes A cathode and a fuel cell using the cathode were manufactured in the same manner as in Example 1, except that the compound of Formula 8 was not used in the manufacture of the cathode. The loading amount of Pt of Pt/Co in the cathode was 1.83 mg/cm2, and the loading amount of Pt in the anode was 0.9 mg/cm2.

Comparative Example 2

Manufacture of Electrodes for Fuel Cells and a Fuel Cell Including the Electrodes A cathode and a fuel cell using the cathode were manufactured in the same manner as in Example 1, except that a compound represented by Formula 61 below was used, instead of the compound of Formula 8, in the manufacture of the cathode. The loading amount of Pt of Pt/Co in the cathode was 1.80 mg/cm2, and the loading amount of platinum (Pt) in the anode was 0.9 mg/cm2.

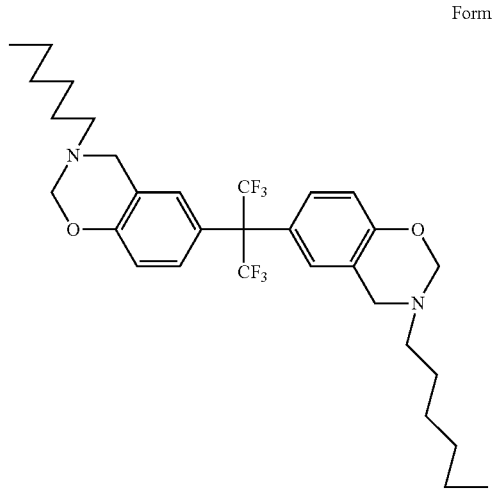

Formula 61

Changes in cell voltages with respect to current density of the fuel cells manufactured in Example 1 and Comparative Example 1 were measured. The results are shown in FIG. 5.

Figure 5:
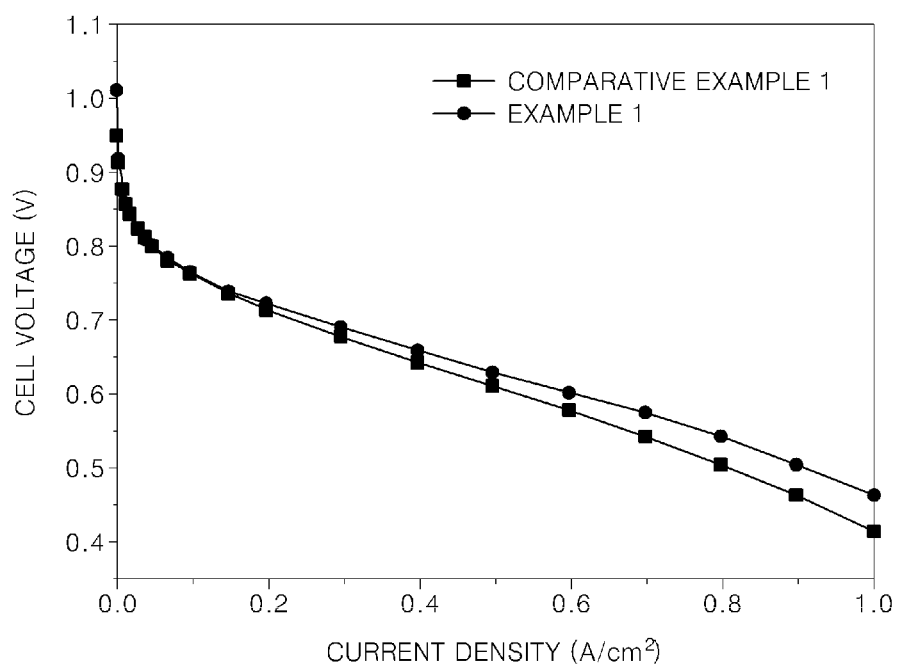
FIG. 5 is a graph of cell voltages with respect to current density of fuel cells manufactured in Example 1 and Comparative Example 1.

Referring to FIG. 5, the fuel cell of Example 1 was found to have better cell voltage characteristics, as compared to the fuel cell of Comparative Example 1.

Changes in cell voltages with respect to time of the fuel cells manufactured in Example 1 and Comparative Example 1 were measured. The results are shown in FIG. 6.

Figure 6:
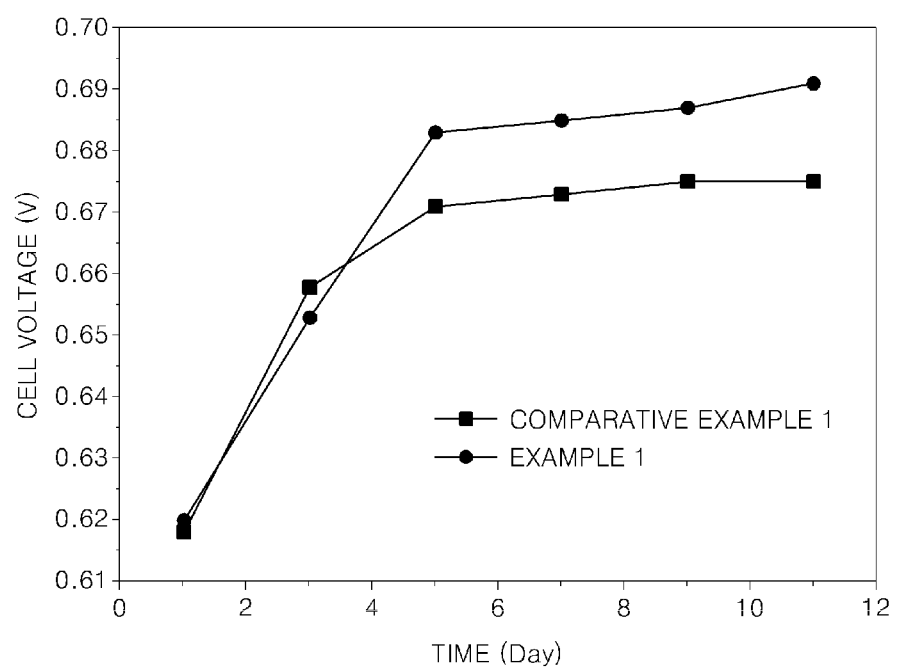
FIG. 6 is a graph of cell voltages with respect to time of the fuel cells manufactured in Example 1 and Comparative Example 1.

Referring to FIG. 6, the fuel cell of Example 1 was found to have better cell voltage characteristics over time, as compared to the fuel cell of Comparative Example 1.

Changes in cell voltages with respect to current density of the fuel cells manufactured in Example 1 and Comparative Examples 1 and 2 were measured. The results are shown in FIG. 7.

Figure 7:
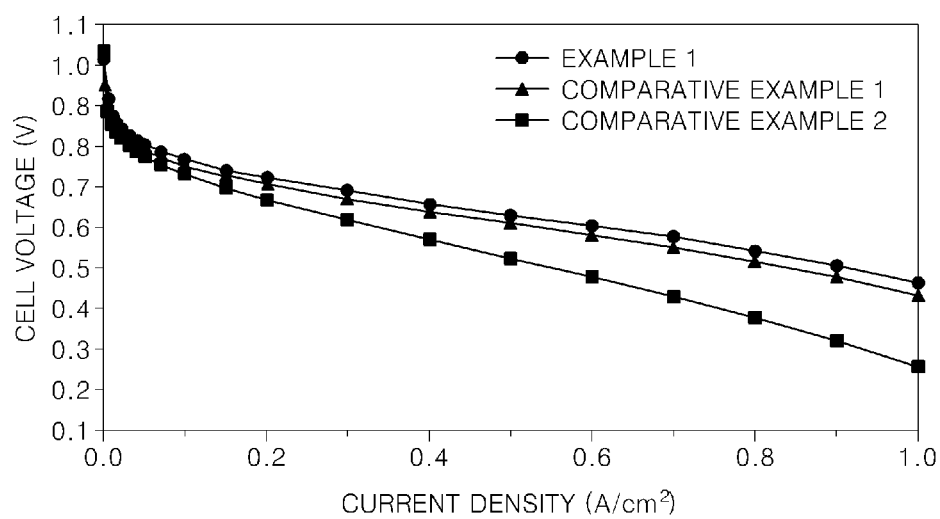
FIG. 7 is a graph of cell voltages with respect to current density of the fuel cells manufactured in Example 1 and Comparative Examples 1 and 2.

Referring to FIG. 7, the fuel cell of Example 1 was found to have better cell voltage characteristics, as compared to the fuel cells of Comparative Examples 1 and 2.

As described above, when a benzoxazine-based monomer composition and a polymer thereof according to the one or more of the above embodiments of the present invention is used to manufacture an electrode of a fuel cell, hydrophobicity of the electrode may be adjusted, thereby increasing oxygen permeability of the electrode. Thus, cell performance may be improved even when air is used in the cathode.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A composition comprising a polymer that is a polymerization product of a composition comprising at least one compound selected from a compound represented by Formula 1 below and a compound represented by Formula 2 below:

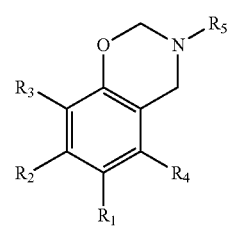

Formula 1

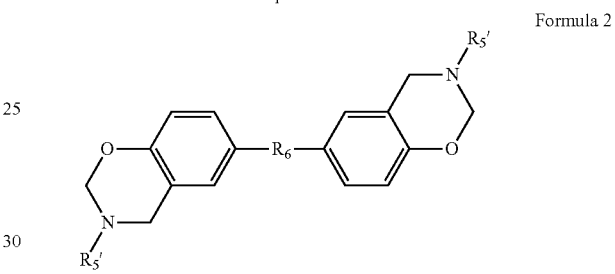

Formula 2 wherein, in Formulae 1 and 2, $R_1$ through $R_4$ are each independently a hydrogen atom, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_2$-$C_{20}$ heteroaryl group, a substituted or unsubstituted $C_2$-$C_{20}$ heteroaryloxy group, a substituted or unsubstituted $C_4$-$C_{20}$ carbocyclic group, a substituted or unsubstituted $C_4$-$C_{20}$ carbocyclic oxy group, a substituted or unsubstituted $C_2$-$C_{20}$ heterocyclic group, a substituted or unsubstituted $C_2$-$C_{20}$ heterocyclicoxy group, a halogen atom, a hydroxyl group, or a cyano group, $R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(═O)—, —O— and —SO$_2$—, and $R_5$ and $R_5'$ are each independently —(CF$_2$)$_n$—CF$_3$ wherein n is an integer from 7 to 15, or the group represented by Formula 3 below, and

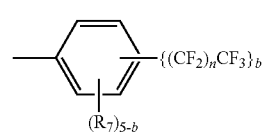

Formula 3 wherein, in Formula 3, n is an integer from 1 to 20, and b is an integer from 1 to 3, and $R_7$ is identical or different from each other and is selected from among a hydrogen atom, fluorine, a $C_1$-$C_{20}$ alkyl group, a fluorinated $C_1$-$C_{20}$ alkyl group, a $C_6$-$C_{20}$ aryl group, and a fluorinated $C_6$-$C_{20}$ aryl group, and wherein the compound of Formula 2 comprises one compound selected from among the compounds represented by Formulae 8, 9, 10 and 11 below:

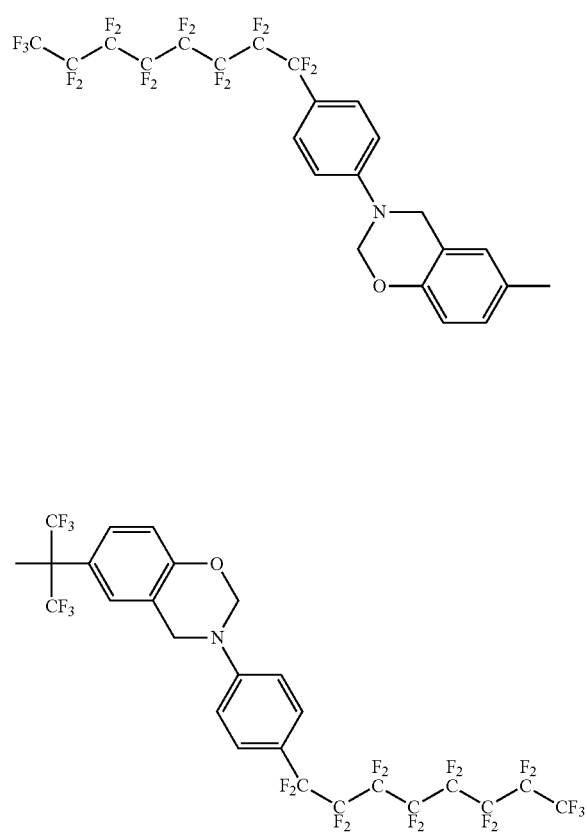

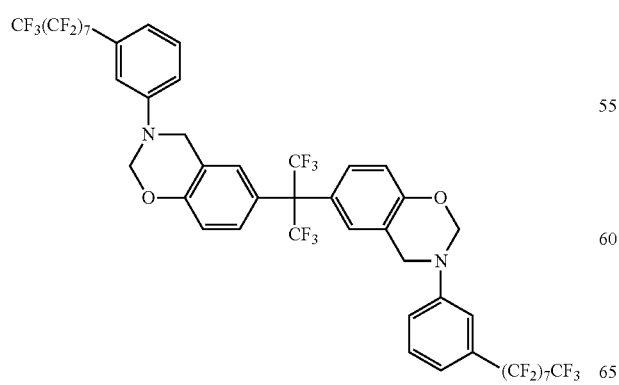

the composition further comprising a cross-linkable compound comprising at least one material selected from the group consisting of a polyazole-based material, a polyoxazole material and a polyimide material.

2. The polymer of claim 1, wherein $R_5$ and $R_5'$ in Formulae 1 and 2 are each independently —$(CF_2)_n$—$CF_3$ wherein n is an integer from 5 to 15, or the group represented by Formula 3 wherein n is an integer from 5 to 15.

3. The polymer of claim 1, wherein the compound of Formula 2 comprises one compound selected from among the compounds represented by Formulae 4, 5, 6 and 7 below:

Formula 5

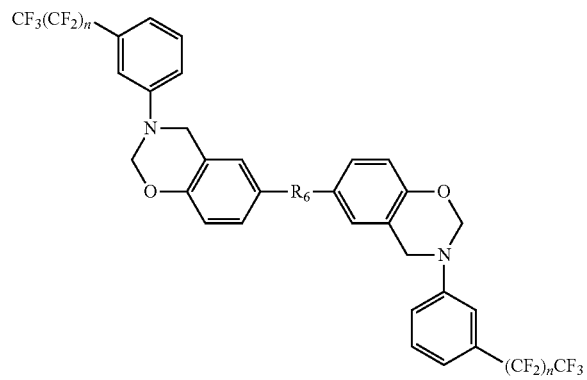

Formula 6

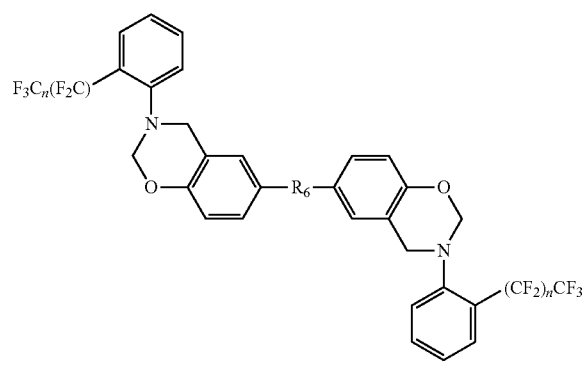

Formula 7

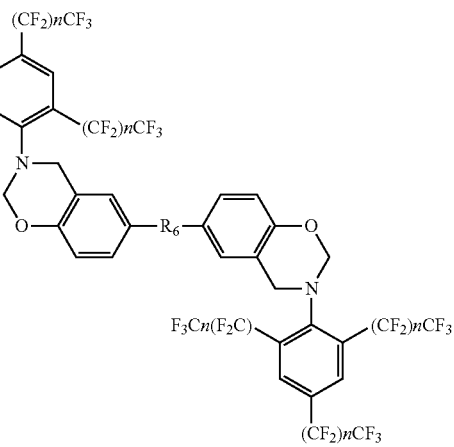

wherein, in Formulae 4-7, n is an integer from 1 to 20, and $R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(=O)—, —O—, and —SO$_2$—.

4. The polymer of claim 1, wherein the compound of Formula 2 comprises one compound selected from among the compounds represented by Formulae 8, 9, 10 and 11 below:

Formula 8

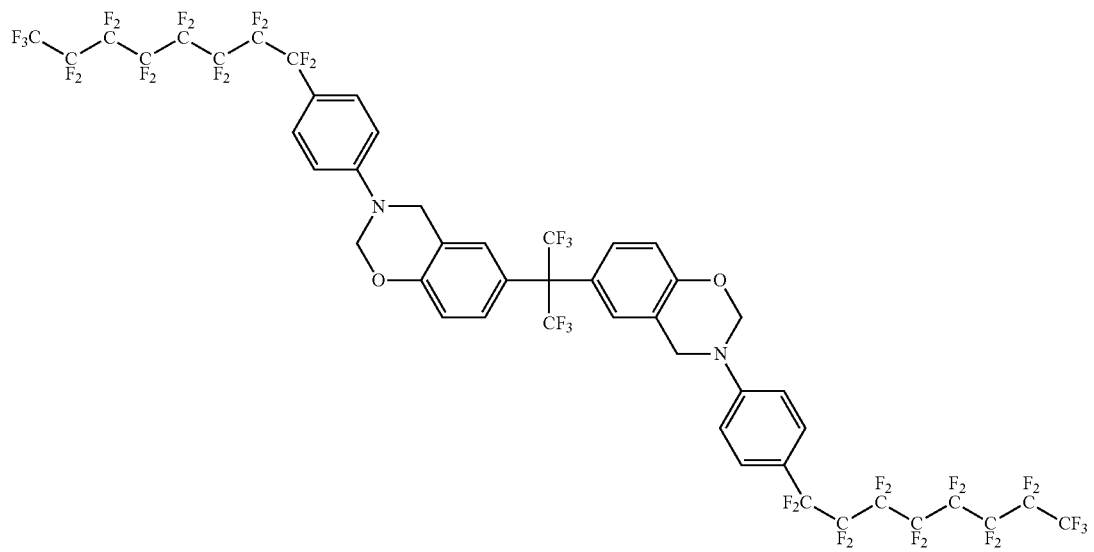

-continued

Formula 9

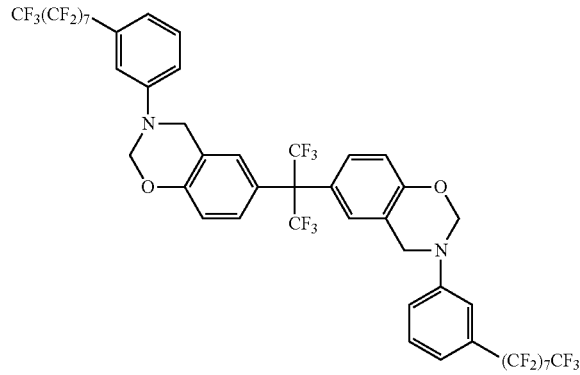

Formula 10

Formula 11

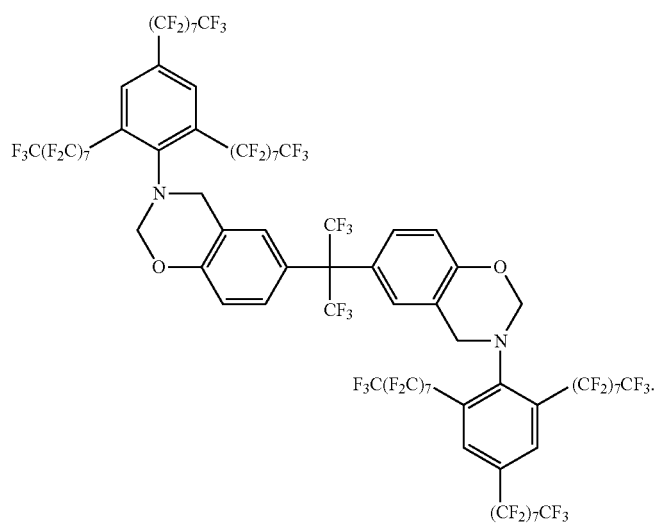

5. The polymer of claim 1, further comprising at least one cross-linkable compound selected from the group consisting of a polyazole-based material, polyimide and polyoxazole.

6. An electrode for a fuel cell, the electrode comprising a composition comprising a polymer that is a polymerization product of a composition comprising at least one compound selected from a compound represented by Formula 1 below and a compound represented by Formula 2 below:

Formula 1

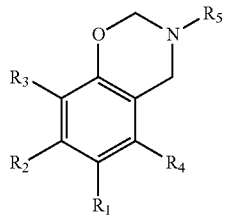

Formula 2

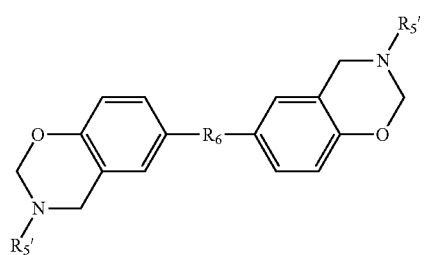

wherein, in Formulae 1 and 2, $R_1$ through $R_4$ are each independently a hydrogen atom, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_2$-$C_{20}$ heteroaryl group, a substituted or unsubstituted $C_2$-$C_{20}$ heteroaryloxy group, a substituted or unsubstituted $C_4$-$C_{20}$ carbocyclic group, a substituted or unsubstituted $C_4$-$C_{20}$ carbocyclic oxy group, a substituted or unsubstituted $C_2$-$C_{20}$ heterocyclic group, a substituted or unsubstituted $C_2$-$C_{20}$ heterocyclicoxy group, a halogen atom, a hydroxyl group, or a cyano group, $R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C_{20}$ heteroarylene group, —C(=O)—, —O— and —SO$_2$—, and $R_5$ and $R_5'$ are each independently —(CF$_2$)$_n$—CF$_3$ wherein n is an integer from 7 to 15, or the group represented by Formula 3 below wherein n is an integer from 1 to 20, and Formula 3

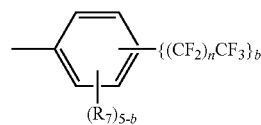

wherein, in Formula 3, n is an integer from 1 to 20, and b is an integer from 1 to 3, and R$_7$ is identical or different from each other and is selected from among a hydrogen atom, fluorine, a $C_1$-$C_{20}$ alkyl group, a fluorinated $C_1$-$C_{20}$ alkyl group, a $C_6$-$C_{20}$ aryl group, and a fluorinated $C_6$-$C_{20}$ aryl group, and wherein the compound of Formula 2 comprises one compound selected from among the compounds represented by Formulae 8, 9, 10 and 11 below:

Formula 8

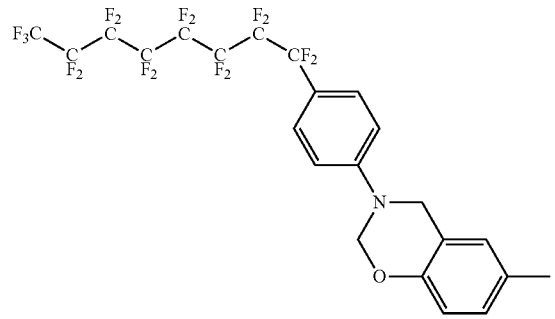

Formula 9

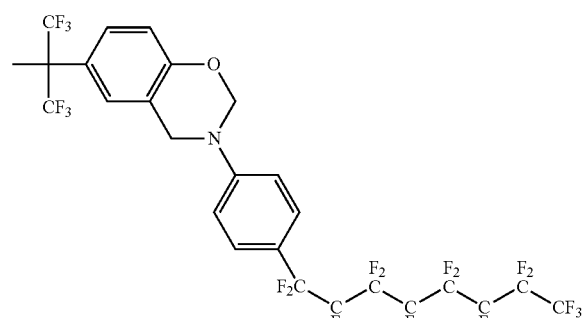

Formula 10

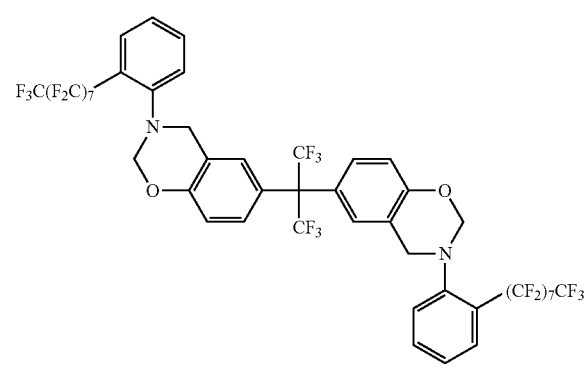

Formula 11

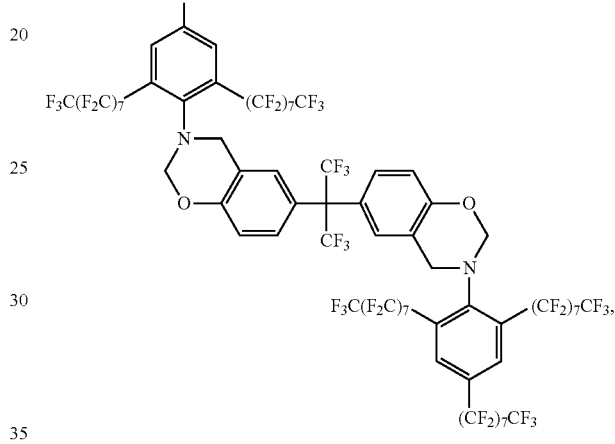

the composition further comprising a cross-linkable compound comprising at least one material selected from the group consisting of a polyazole-based material, a polyoxazole material and a polyimide material.

7. The electrode of claim 6, comprising a catalyst layer including the polymer and a catalyst.

8. The electrode of claim 7, wherein the amount of the polymer in the catalyst layer is in the range of about 0.001 parts to about 0.5 parts by weight based on 1 part by weight of the catalyst.

9. The electrode of claim 5, wherein R$_5$ and R$_5$' in Formulae 1 and 2 are each independently —(CF$_2$)$_n$—CF$_3$ wherein n is an integer from 5 to 15, or the group represented by Formula 3 wherein n is an integer from 5 to 15.

10. The electrode of claim 6, wherein the compound of Formula 2 comprises one compound selected from among the compounds represented by Formulae 4, 5, 6 and 7 below:

Formula 4

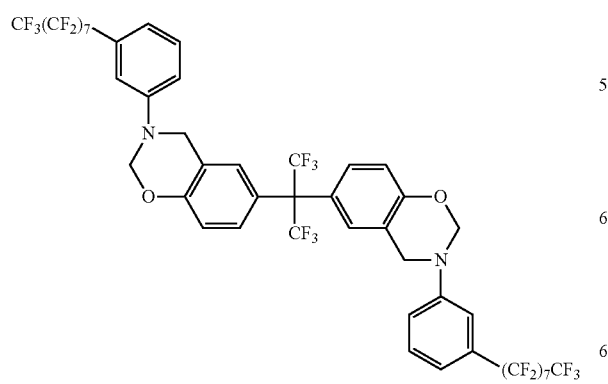

Formula 5

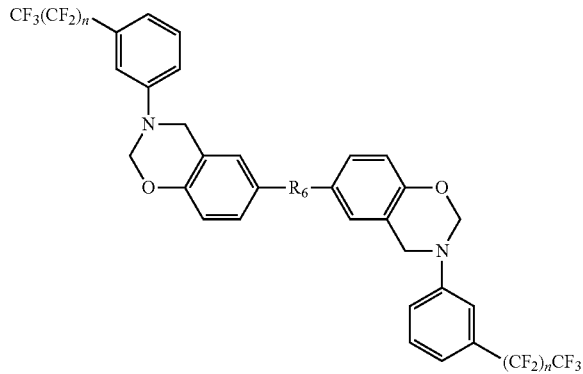

Formula 6

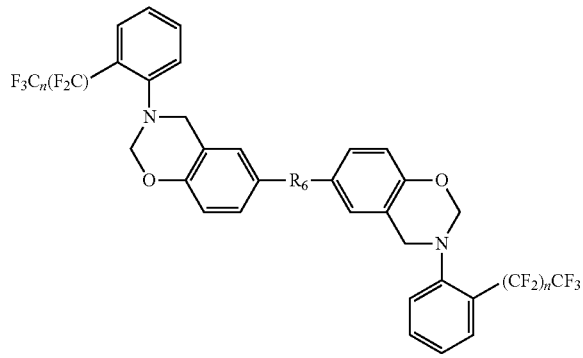

Formula 7

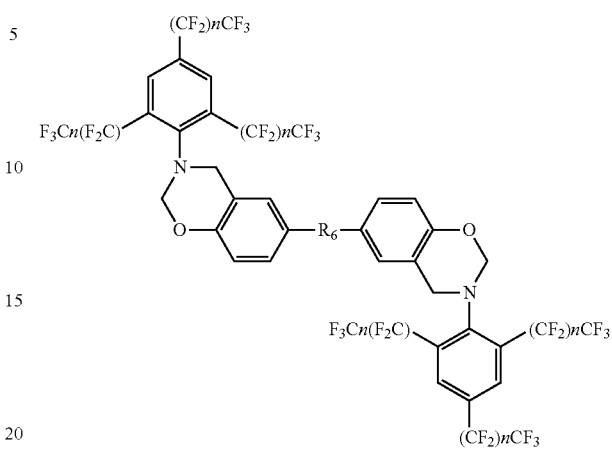

wherein, in Formulae 4-7, n is an integer from 1 to 20, and $R_6$ is selected from the group consisting of a substituted or unsubstituted $C_1$-$C_{20}$ alkylene group, a substituted or unsubstituted $C_2$-$C_{20}$ alkenylene group, a substituted or unsubstituted $C_2$-$C_{20}$ alkynylene group, a substituted or unsubstituted $C_6$-$C_{20}$ arylene group, a substituted or unsubstituted $C_2$-$C^{20}$ heteroarylene group, —C(=O)—, —O—, and —SO$_2$—.

11. The electrode of claim 6, wherein the compound of Formula 2 comprises one compound selected from among the compounds represented by Formulae 8, 9, 10 and 11 below:

Formula 8

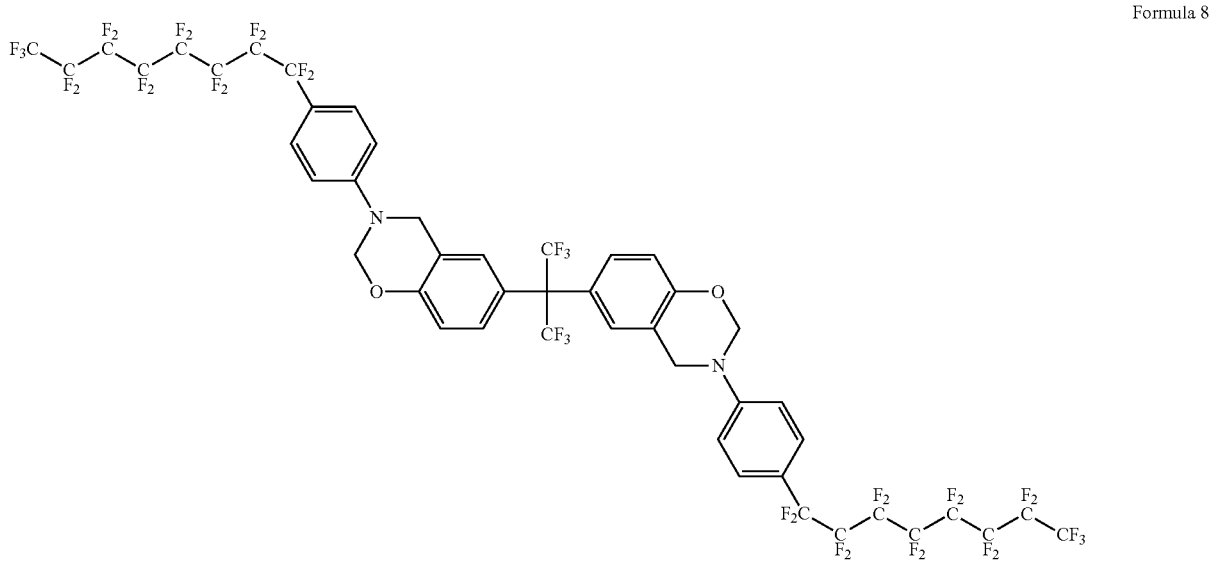

-continued

Formula 9

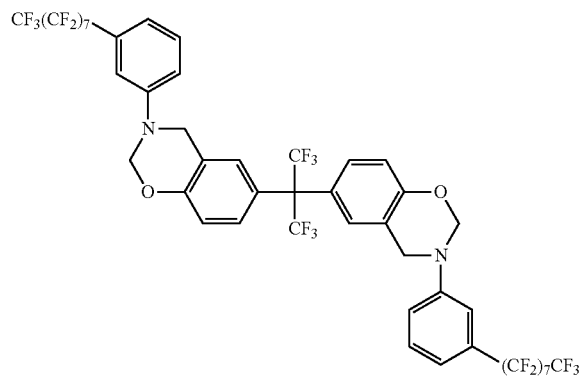

Formula 10

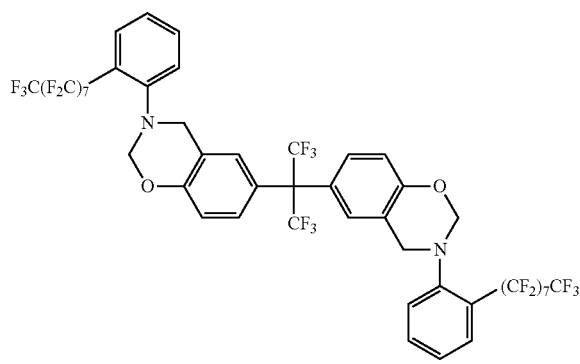

Formula 11

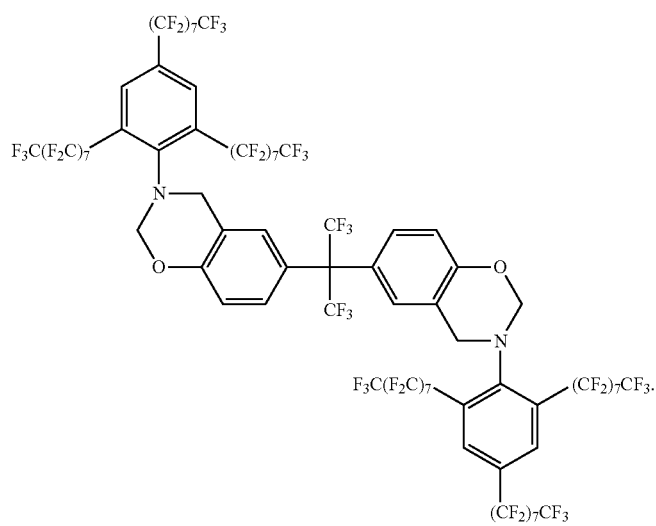

12. The electrode of claim 6, further comprising at least one cross-linkable compound selected from the group consisting of a polyazole-based material, polyimide and polyoxazole.

13. An electrolyte membrane for a fuel cell, the electrolyte membrane comprising a polymer that is a polymerization product of the composition of claim 1.

14. The electrolyte membrane of claim 13, further comprising a proton conductor.

15. The electrolyte membrane of claim 14, wherein the proton conductor comprises a phosphoric acid or a $C_1$-$C_{20}$ organic phosphonic acid.

16. A fuel cell comprising:
a cathode;
an anode; and
an electrolyte membrane disposed between the cathode and the anode,
wherein at least one of the cathode, the anode and the electrolyte membrane comprises a polymer that is a polymerization product of the composition of claim 1.

* * * * *